United States Patent
Fisher et al.

(10) Patent No.: US 11,913,067 B2
(45) Date of Patent: Feb. 27, 2024

(54) COMPOSITIONS AND METHODS FOR AMPLIFYING POLYNUCLEOTIDES

(71) Applicants: ILLUMINA, INC., San Diego, CA (US); ILLUMINA CAMBRIDGE LIMITED, Cambridge (GB)

(72) Inventors: Jeffrey Fisher, San Diego, CA (US); Jason Betley, Buntingford (GB)

(73) Assignees: Illumina, Inc., San Diego, CA (US); Illumina Cambridge Limited, Cambridge (GB)

(*) Notice: Subject to any disclaimer, the term of this patent is extended or adjusted under 35 U.S.C. 154(b) by 239 days.

(21) Appl. No.: 17/459,966

(22) Filed: Aug. 27, 2021

(65) Prior Publication Data
US 2022/0090187 A1      Mar. 24, 2022

Related U.S. Application Data

(60) Provisional application No. 63/077,857, filed on Sep. 14, 2020.

(51) Int. Cl.
C12Q 1/6855       (2018.01)
C12Q 1/6837       (2018.01)

(52) U.S. Cl.
CPC ......... *C12Q 1/6855* (2013.01); *C12Q 1/6837* (2013.01)

(58) Field of Classification Search
CPC .................................................. C12Q 1/6837
See application file for complete search history.

(56) References Cited

U.S. PATENT DOCUMENTS

| | | |
|---|---|---|
| 10,385,384 B2 | 8/2019 | Shen et al. |
| 10,619,204 B2 | 4/2020 | Gunderson et al. |
| 2012/0122737 A1* | 5/2012 | Sabot ................... C12Q 1/6806 506/40 |

FOREIGN PATENT DOCUMENTS

| | | |
|---|---|---|
| WO | 2007010254 A1 | 1/2007 |
| WO | 2011025477 A1 | 3/2011 |
| WO | 2012025250 A1 | 3/2012 |
| WO | 2015189637 A1 | 12/2015 |
| WO | 2016075204 A1 | 5/2016 |
| WO | 2018128777 A1 | 7/2018 |

OTHER PUBLICATIONS

International Search Report and Written Opinion for PCT/US2021/048064 dated Feb. 11, 2022; 21 pages.

* cited by examiner

*Primary Examiner* — Teresa E Strzelecka
(74) *Attorney, Agent, or Firm* — Snell & Wilmer, L.L.P.; Jaime D. Choi; Jonathan B. Fitzgerald

(57) ABSTRACT

A composition for amplifying a polynucleotide is provided that includes a substrate comprising a first region and a second region. A first plurality of capture primers is coupled to the first region of the substrate. A second plurality of capture primers is coupled to the second region of the substrate. The capture primers of the second plurality of capture primers are longer than the capture primers of the first plurality of capture primers. A first plurality of orthogonal capture primers are coupled to the first region of the substrate. A second plurality of orthogonal capture primers are coupled to the second region of the substrate. The orthogonal capture primers of the second plurality of orthogonal capture primers are shorter than the orthogonal capture primers of the first plurality of orthogonal capture primers.

20 Claims, 19 Drawing Sheets
Specification includes a Sequence Listing.

COMPOSITIONS AND METHODS FOR AMPLIFYING POLYNUCLEOTIDES

CROSS-REFERENCE TO RELATED APPLICATIONS

This application claims the benefit of U.S. Provisional Patent Application No. 63/077,857, filed Sep. 14, 2020 and entitled "Compositions and Methods for Amplifying Polynucleotides," the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Aug. 27, 2021, is named IP-1997-US_93632-0064_SL.txt and is 2,136 bytes in size.

BACKGROUND

Cluster amplification is an approach to amplifying polynucleotides, for example for use in genetic sequencing. Target polynucleotides are captured by primers (e.g., P5 and P7 primers) coupled to a substrate surface in a flowcell, and form "seeds" at random locations on the surface. Cycles of amplification are performed to form clusters on the surface around each seed. The clusters include copies, and complementary copies, of the seed polynucleotides. In some circumstances, the substrate is patterned so as to define regions that bound different clusters, such as wells that may be filled with respective clusters.

SUMMARY

Examples provided herein are related to amplifying polynucleotides. Compositions and methods for performing such amplification are disclosed.

In some examples, a composition for amplifying a polynucleotide is provided. The composition may include a substrate including a first region and a second region; a first plurality of capture primers coupled to the first region of the substrate; and a second plurality of capture primers coupled to the second region of the substrate. The capture primers of the second plurality of capture primers may be longer than the capture primers of the first plurality of capture primers. The composition also may include a first plurality of orthogonal capture primers coupled to the first region of the substrate; and a second plurality of orthogonal capture primers coupled to the second region of the substrate. The orthogonal capture primers of the second plurality of orthogonal capture primers may be shorter than the orthogonal capture primers of the first plurality of orthogonal capture primers.

In some examples, the first adapter of a first one of the target polynucleotides is hybridized to a first one of the orthogonal capture primers of the first plurality of orthogonal capture primers, or the second adapter of the first one of the target polynucleotides is hybridized to a first one of the capture primers of the second plurality of capture primers. In some examples, a duplex formed from the hybridization between the first adapter of the first one of the target polynucleotides and the first one of the orthogonal capture primers has a melting temperature (Tm) of greater than about 40° C.

In some examples, the composition further includes a first amplicon covalently coupled to one of the orthogonal capture primers of the first plurality of orthogonal capture primers, the first amplicon having a second adapter completely hybridized to one of the capture primers of the second plurality of capture primers.

In some examples, the composition further includes a second amplicon covalently coupled to one of the capture primers of the first plurality of capture primers, the second amplicon having a first adapter completely hybridized to one of the orthogonal capture primers of the second plurality of orthogonal capture primers.

In some examples, the composition further includes a third amplicon covalently coupled to one of the orthogonal capture primers of the first plurality of orthogonal capture primers, the third amplicon having a second adapter that is unable to completely hybridize to any of the capture primers of the first plurality of capture primers. The inability of the second adapter to completely hybridize to any of the capture primers of the first plurality of capture primers may, in some examples, inhibit amplification of the third amplicon. In some examples, any partial duplex between the second adapter of the third amplicon and any of the capture primers of the first plurality of capture primers has a melting temperature (Tm) of less than about 20° C.

In some examples, the composition further includes a fourth amplicon covalently coupled to one of the capture primers of the second plurality of capture primers, the fourth amplicon having a first adapter that is unable to completely hybridize to any of the orthogonal capture primers of the second plurality of orthogonal capture primers. In some examples, the inability of the first adapter to completely hybridize to any of the orthogonal capture primers of the second plurality of orthogonal capture primers inhibits amplification of the fourth amplicon.

In some examples, the capture primers of the second plurality of capture primers are P5 capture primers, and the orthogonal capture primers of the first plurality of orthogonal capture primers are P7 capture primers. In some examples, the capture primers of the first plurality of capture primers are shortened P5 capture primers, and the orthogonal capture primers of the second plurality of orthogonal capture primers are shortened P7 capture primers.

In some examples, the capture primers of the first plurality of capture primers are at least 5 bases shorter than the capture primers of the second plurality of capture primers, and the orthogonal capture primers of the second plurality of orthogonal capture primers are at least 5 bases shorter than the orthogonal capture primers of the first plurality of orthogonal capture primers.

In some examples, the capture primers of the first plurality of capture primers are approximately the same length as the orthogonal capture primers of the second plurality of capture primers. In some examples, the capture primers of the second plurality of capture primers are approximately the same length as the orthogonal capture primers of the first plurality of capture primers.

In some examples, the first region of the substrate is adjacent to the second region of the substrate. In some examples, the first region of the substrate surrounds the second region of the substrate. In some examples, the second region of the substrate surrounds the first region of the substrate.

In some examples, another composition for amplifying a polynucleotide is provided. The composition may include a substrate including a first region and a second region; a first plurality of capture primers coupled to the first region of the substrate; and a first plurality of orthogonal capture primers coupled to the first region of the substrate. The composition also may include a second plurality of capture primers coupled to the second region of the substrate; a second plurality of orthogonal capture primers coupled to the second region of the substrate; a first plurality of removable blocking groups coupled to the capture primers of the second plurality of capture primers; and a second plurality of removable blocking groups coupled to the orthogonal capture primers of the second plurality of capture primers.

In some examples, the composition further includes a fluid including target polynucleotides, each of the target polynucleotides including a first adapter that is complementary to the orthogonal capture primers of the first and second pluralities of orthogonal capture primers, and a second adapter that is complementary to the capture primers of the first and second pluralities of capture primers. In some examples, the first adapters of the target polynucleotides are about the same length as the capture primers of the first and second pluralities of capture primers, and the second adapters of the target polynucleotides are about the same length as the orthogonal capture primers of the second plurality of orthogonal capture primers.

In some examples, the first adapter of a first one of the target polynucleotides is hybridized to one of the orthogonal capture primers of the first plurality of orthogonal capture primers, or the second adapter of the first one of the target polynucleotides is hybridized to one of the capture primers of the first plurality of capture primers. In some examples, a duplex formed from the hybridization between the second adapter of the first one of the target polynucleotides and the one of the capture primers has a melting temperature (Tm) of greater than about 40° C., or a duplex formed from the hybridization between the first adapter of the first one of the target polynucleotides and the one of the orthogonal capture primers has a melting temperature (Tm) of greater than about 40° C.

In some examples, the first adapter of a second one of the target polynucleotides is hybridized to one of the orthogonal capture primers of the second plurality of orthogonal capture primers, or the second adapter of the second one of the target polynucleotides is hybridized to one of the capture primers of the second plurality of capture primers. In some examples, the removable blocking group coupled to the one of the capture primers inhibits amplification of the second one of the target polynucleotides, or the removable blocking group coupled to the one of the orthogonal capture primers inhibits amplification of the second one of the target polynucleotides.

In some examples, the composition further includes an amplicon covalently coupled to one of the orthogonal capture primers of the first plurality of orthogonal capture primers, the amplicon having a second adapter completely hybridized to one of the capture primers of the first plurality of capture primers.

In some examples, the composition further includes an amplicon covalently coupled to one of the capture primers of the first plurality of capture primers, the amplicon having a first adapter completely hybridized to one of the orthogonal capture primers of the first plurality of orthogonal capture primers.

In some examples, the capture primers of the first and second pluralities of capture primers are P5 capture primers, and the orthogonal capture primers of the first and second pluralities of orthogonal capture primers are P7 capture primers.

In some examples, the capture primers of the first plurality of capture primers are approximately the same length as the capture primers of the second plurality of capture primers. In some examples, the capture primers of the second plurality of capture primers are approximately the same length as the orthogonal capture primers of the first plurality of orthogonal capture primers.

In some examples, the first region of the substrate is adjacent to the second region of the substrate. In some examples, the first region of the substrate surrounds the second region of the substrate. In some examples, the second region of the substrate surrounds the first region of the substrate.

In some examples, a method for amplifying a polynucleotide is provided. The method includes contacting a composition with a fluid. The composition may include a substrate including a first region and a second region; a first plurality of capture primers coupled to the first region of the substrate; and a second plurality of capture primers coupled to the second region of the substrate. The capture primers of the second plurality of capture primers may be longer than the capture primers of the first plurality of capture primers. The composition also may include a first plurality of orthogonal capture primers coupled to the first region of the substrate; and a second plurality of orthogonal capture primers coupled to the second region of the substrate. The orthogonal capture primers of the second plurality of orthogonal capture primers may be shorter than the orthogonal capture primers of the first plurality of orthogonal capture primers. The fluid may include target polynucleotides, each of the target polynucleotides including a first adapter that is complementary to the orthogonal capture primers of the first and second pluralities of orthogonal capture primers, and a second adapter that is complementary to the capture primers of the first and second pluralities of capture primers. The method may include hybridizing the first adapter of a first one of the target polynucleotides to an orthogonal capture primer of the first or second pluralities of orthogonal capture primers, or hybridizing the second adapter of that target polynucleotide to a capture primer of the first or second pluralities of capture primers; and then amplifying the first one of the target polynucleotides, the amplifying comprising generating amplicons of the first one of the target polynucleotides.

In some examples, the first adapters of the target polynucleotides are shorter than the orthogonal capture primers of the first plurality of orthogonal capture primers, and the second adapters of the target polynucleotides are shorter than the capture primers of the second plurality of capture primers.

In some examples, a duplex formed from the hybridization between the first adapter of the first one of the target polynucleotides and the first one of the orthogonal capture primers has a melting temperature (Tm) of greater than about 40° C. In some examples, the amplicon is hybridized to the first one of the target polynucleotides. In some examples, the method includes dehybridizing the first one of the target polynucleotides, and then amplifying the amplicon.

In some examples, the method includes covalently coupling a first amplicon to one of the orthogonal capture primers of the first plurality of orthogonal capture primers, and completely hybridizing a second adapter of the first amplicon to one of the capture primers of the second plurality of capture primers.

In some examples, the method includes covalently coupling a second amplicon to one of the capture primers of the first plurality of capture primers, and completely hybridizing a first adapter of the second amplicon to one of the orthogonal capture primers of the second plurality of orthogonal capture primers.

In some examples, the method includes covalently coupling a third amplicon to one of the orthogonal capture primers of the first plurality of orthogonal capture primers, and being unable to completely hybridize a second adapter of the third amplicon to any of the capture primers of the first plurality of capture primers. In some examples, the inability of the second adapter to completely hybridize to any of the capture primers of the first plurality of capture primers inhibits amplification of the third amplicon. In some examples, any partial duplex between the second adapter of the third amplicon and any of the capture primers of the first plurality of capture primers has a melting temperature (Tm) of less than about 20° C.

In some examples, the method includes covalently coupling a fourth amplicon to one of the capture primers of the second plurality of capture primers, and being unable to completely hybridize a first adapter of the fourth amplicon to any of the orthogonal capture primers of the second plurality of orthogonal capture primers. In some examples, the inability of the first adapter to completely hybridize to any of the orthogonal capture primers of the second plurality of orthogonal capture primers inhibits amplification of the fourth amplicon.

In some examples, the capture primers of the second plurality of capture primers are P5 capture primers, and the orthogonal capture primers of the first plurality of orthogonal capture primers are P7 capture primers. In some examples, the capture primers of the first plurality of capture primers are shortened P5 capture primers, and the orthogonal capture primers of the second plurality of orthogonal capture primers are shortened P7 capture primers. In some examples, the capture primers of the first plurality of capture primers are at least 5 bases shorter than the capture primers of the second plurality of capture primers, and the orthogonal capture primers of the second plurality of orthogonal capture primers are at least 5 bases shorter than the orthogonal capture primers of the first plurality of orthogonal capture primers. In some examples, the capture primers of the first plurality of capture primers are approximately the same length as the orthogonal capture primers of the second plurality of capture primers. In some examples, the capture primers of the second plurality of capture primers are approximately the same length as the orthogonal capture primers of the first plurality of capture primers.

In some examples, the first region of the substrate is adjacent to the second region of the substrate. In some examples, the first region of the substrate surrounds the second region of the substrate. In some examples, the second region of the substrate surrounds the first region of the substrate.

In some examples, another method for amplifying a polynucleotide is provided. The method may include contacting a composition with a fluid. The composition may include a substrate including a first region and a second region; a first plurality of capture primers coupled to the first region of the substrate; and a first plurality of orthogonal capture primers coupled to the first region of the substrate. The composition further may include a second plurality of capture primers coupled to the second region of the substrate; a second plurality of orthogonal capture primers coupled to the second region of the substrate; a first plurality of removable blocking groups coupled to the capture primers of the second plurality of capture primers; and a second plurality of removable blocking groups coupled to the orthogonal capture primers of the second plurality of capture primers. The fluid may include target polynucleotides, each of the target polynucleotides including a first adapter that is complementary to the orthogonal capture primers of the first and second pluralities of orthogonal capture primers, and a second adapter that is complementary to the capture primers of the first and second pluralities of capture primers. The method may include hybridizing the first adapter of a first one of the target polynucleotides to a first one of the orthogonal capture primers of the first plurality of orthogonal capture primers, or hybridizing the second adapter of the first one of the target polynucleotides to a first one of the capture primers of the first plurality of capture primers. The method may include amplifying the first one of the target polynucleotides, the amplifying including generating a first amplicon of the first one of the target polynucleotides in the first region of the substrate. The method may include removing the first and second pluralities of removable blocking groups; and then further amplifying the first one of the target polynucleotides, the amplifying including generating additional amplicons of the first one of the target polynucleotides in the second region of the substrate.

In some examples, the first adapters of the target polynucleotides are about the same length as the orthogonal capture primers of the first and second pluralities of orthogonal capture primers, and the second adapters of the target polynucleotides are about the same length as the capture primers of the first and second pluralities of capture primers.

In some examples, a duplex formed from the hybridization between the second adapter of the first one of the target polynucleotides and the one of the capture primers has a melting temperature (Tm) of greater than about 40° C., or wherein a duplex formed from the hybridization between the first adapter of the first one of the target polynucleotides and the one of the orthogonal capture primers has a melting temperature (Tm) of greater than about 40° C.

In some examples, the first adapter of a second one of the target polynucleotides is hybridized to one of the orthogonal capture primers of the second plurality of orthogonal capture primers, or wherein the second adapter of the second one of the target polynucleotides is hybridized to one of the capture primers of the second plurality of capture primers. In some examples, the removable blocking group coupled to the one of the capture primers inhibits amplification of the second one of the target polynucleotides, or wherein the removable blocking group coupled to the one of the orthogonal capture primers inhibits amplification of the second one of the target polynucleotides.

In some examples, the method further includes covalently coupling an amplicon to one of the orthogonal capture primers of the first plurality of orthogonal capture primers, the amplicon having a second adapter completely hybridized to one of the capture primers of the first plurality of capture primers.

In some examples, the method further includes covalently coupling an amplicon to one of the capture primers of the first plurality of capture primers, the amplicon having a first adapter completely hybridized to one of the orthogonal capture primers of the first plurality of orthogonal capture primers.

In some examples, the capture primers of the first and second pluralities of capture primers are P5 capture primers, and the orthogonal capture primers of the first and second pluralities of orthogonal capture primers are P7 capture primers. In some examples, the capture primers of the first plurality of capture primers are approximately the same length as the capture primers of the second plurality of capture primers. In some examples, the capture primers of the second plurality of capture primers are approximately the same length as the orthogonal capture primers of the first plurality of orthogonal capture primers.

In some examples, the first region of the substrate is adjacent to the second region of the substrate. In some examples, the first region of the substrate surrounds the second region of the substrate. In some examples, the second region of the substrate surrounds the first region of the substrate.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

DETAILED DESCRIPTION

Examples provided herein are related to amplifying polynucleotides. Compositions and methods for performing such amplification are disclosed.

The monoclonality of a cluster resulting from amplification of target polynucleotide(s) may affect the ease with which the target polynucleotide(s) in that cluster subsequently may be sequenced, e.g., using sequencing-by-synthesis (SBS). Polynucleotides having the same sequence as each other are considered to be "monoclonal," while polynucleotides having different sequences are considered to be "polyclonal." The greater the monoclonality of a cluster— that is, the greater the number of polynucleotides having the same sequence as each other in that cluster—the greater the likelihood that a signal from the ensemble of polynucleotides within that cluster will be sufficient to correctly sequence the polynucleotide having the greatest number amplicons using SBS. A cluster with a number of amplicons of the same polynucleotide sufficient to correctly sequence that polynucleotide is considered to be "functionally monoclonal," even if that cluster may be polyclonal. Illustratively, a cluster from which about 60% or more of the SBS signal comes from amplicons of a particular polynucleotide, and from which about 40% or less of the SBS signal comes from amplicons of one or more other polynucleotides, may be functionally monoclonal, and as such may be accurately sequenced using SBS. In some examples, the amount of SBS signal scales approximately linearly with the amount of a polynucleotide, and as such a cluster with about 60% or more of amplicons of a particular polynucleotide, and with about 40% or less of amplicons of one or more other polynucleotides, may be functionally monoclonal.

Figure 1A:
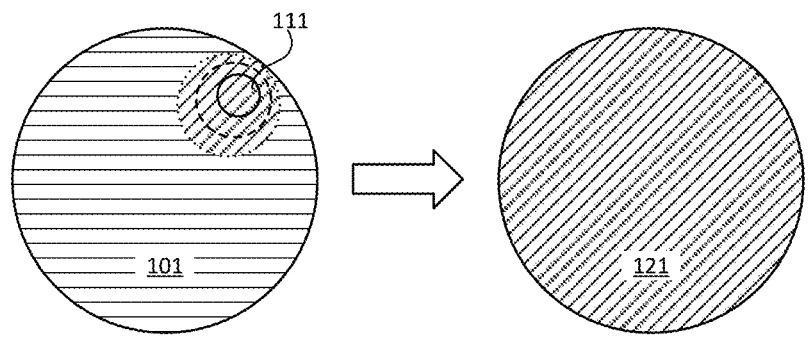
FIGS. 1A-1C schematically illustrate examples of amplifying polynucleotides on a substrate.
Figure 1B:
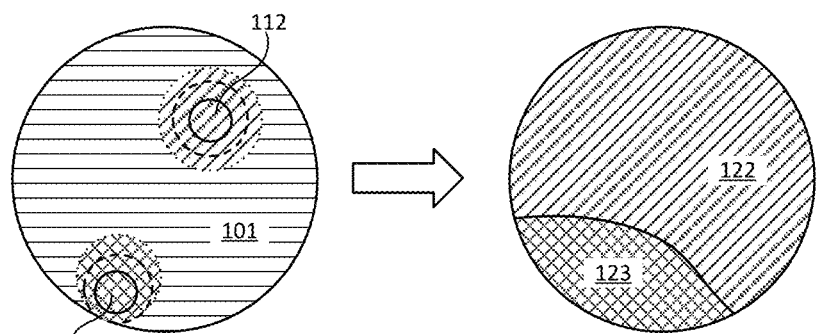
Figure 1C:
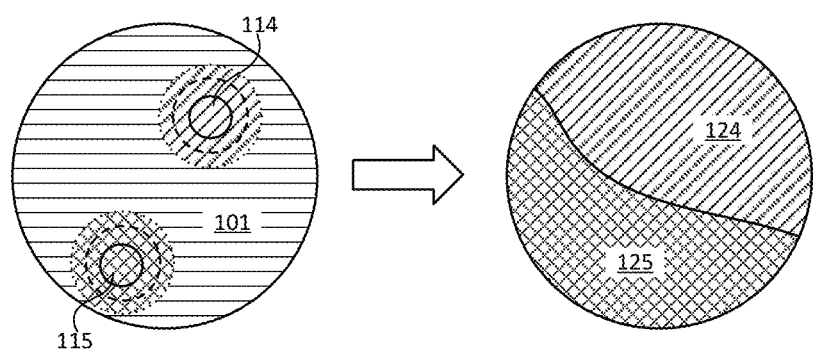

The extent to which a given cluster is monoclonal may relate to a number of factors. For example, FIGS. 1A-1C schematically illustrate examples of amplifying polynucleotides on a substrate. As shown in FIG. 1A, capture and amplification of a single seed 111 on substrate region 101 may result in monoclonal cluster 121 which may fill the substrate region, and which readily may be used for SBS (the dashed and dotted circles being intended to represent expansion of the cluster over time). In comparison, as shown in FIG. 1B, capture and amplification of two seeds 112, 113 on substrate region 101 may result in a polyclonal cluster having a first region 122 resulting from amplification of seed 112, and a second region 123 resulting from amplification of seed 113. In this example, the extent to which the cluster is polyclonal may be sufficiently low that the cluster may be useful for SBS. For example, about 60% or more of the signal from substrate region 101 may be from the amplicons of seed 112 in first region 122 and about 40% or less of the signal from substrate region 101 may be from the amplicons of seed 113 in second region 123. For example, about 60% or more of substrate region 101 may be covered by the amplicons of seed 112 in first region 122 and about 40% or less of substrate region 101 may be covered by amplicons of seed 113 in second region 123. As such the polyclonal cluster 122, 123 may be functionally monoclonal.

However, the relative locations of different seeds on the substrate may affect the extent to which the cluster is polyclonal, and the extent to which the cluster may be useable for SBS. For example, as shown in FIG. 1C, capture and amplification of two seeds 114, 115 on substrate region 101 results in a polyclonal cluster having a first region 124 resulting from amplification of seed 112, and a second region 125 resulting from amplification of seed 115, but second region 125 is larger than second region 123 in FIG. 1B because seed 115 is more centrally located than is seed 113. For example, less than about 60% of the signal from substrate region 101 may be from the amplicons of seed 114 in first region 124 and greater than about 40% of the signal from substrate region 101 may be from the amplicons of seed 115 in second region 125, and as such the polyclonal cluster 124, 125 may not be functionally monoclonal. For example, less than about 60% of substrate region 101 may be covered by amplicons of seed 114 in first region 124 and greater than about 40% of substrate region 101 may be covered by amplicons of seed 115 in second region 125. As such the polyclonal cluster 124, 125 may not be functionally monoclonal. In this example, the extent to which the cluster is polyclonal may be too high for the cluster to be useful for SBS.

Figure 2A:
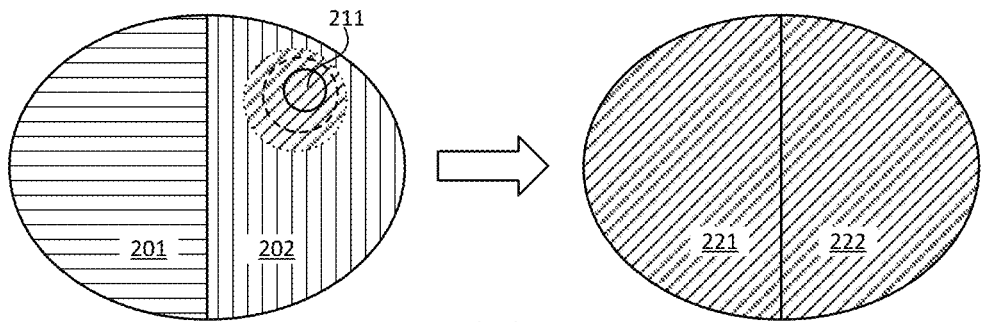
FIGS. 2A-2D schematically illustrate additional examples of amplifying polynucleotides on a substrate.

The number of seeds that may be expected to land on a given substrate region may increase with the size of the substrate. Substrate patterning may further affect the extent to which clusters are polyclonal and the extent to which such clusters are useful for SBS. For example, FIGS. 2A-2D schematically illustrate additional examples of amplifying polynucleotides on a substrate. The substrate may include a first region 201 and second region 202, which may have different surface treatments than one another in a manner such as described with reference to FIG. 3A. It may be desired to perform simultaneous paired-end reads on copies of the same target polynucleotide in both of regions 201, 202 so as to enhance reliability of the read, e.g., by performing SBS reads on the copies in a first direction in region 201 and in the opposite direction in region 202, and then using software to align the results, which should be complementary to one another and thus indicate the same sequence as one another. As shown in FIG. 2A, capture and amplification of a single seed 211 on substrate region 202 (or, equivalently, substrate region 201) results in monoclonal clusters in first region 221 and in second region 222, which may fill both substrate regions, and which readily may be used for simultaneous paired-end reads.

Figure 2B:
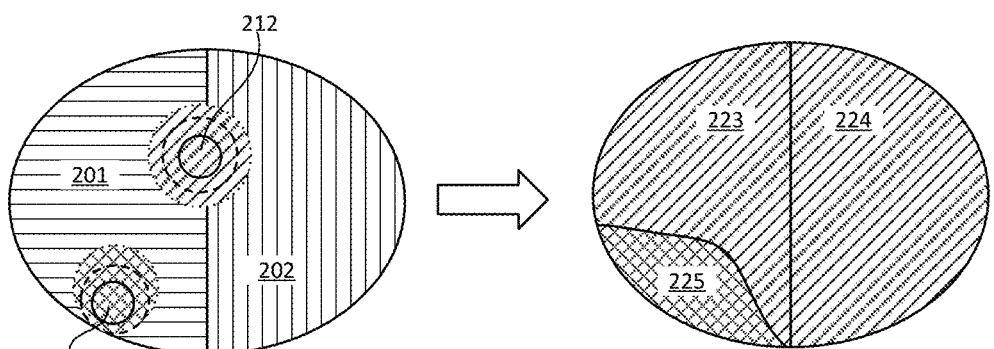

In comparison, as shown in FIG. 2B, capture and amplification of a first seed 212 bridging substrate regions 201, 202 and a second seed 213 on substrate region 201 results in a polyclonal cluster within substrate region 201 that has a first region 223 resulting from amplification of seed 212 within substrate region 201, and a second region 225 resulting from amplification of seed 213 within substrate region 201; and a monoclonal cluster 224 within substrate region 202 resulting from amplification of seed 212 within substrate region 202. In this example, the extent to which a cluster is polyclonal is sufficiently low that substrate region 201 may be functionally monoclonal. As such, regions 201 and 202 together may be functionally monoclonal, and the clusters 223, 224 may be useful for simultaneous paired-end reads. For example, for simultaneous-paired end reads, it may be useful for both substrate regions to independently be at least functionally monoclonal, and for both substrate regions taken together also to be at least functionally monoclonal.

Figure 2C:
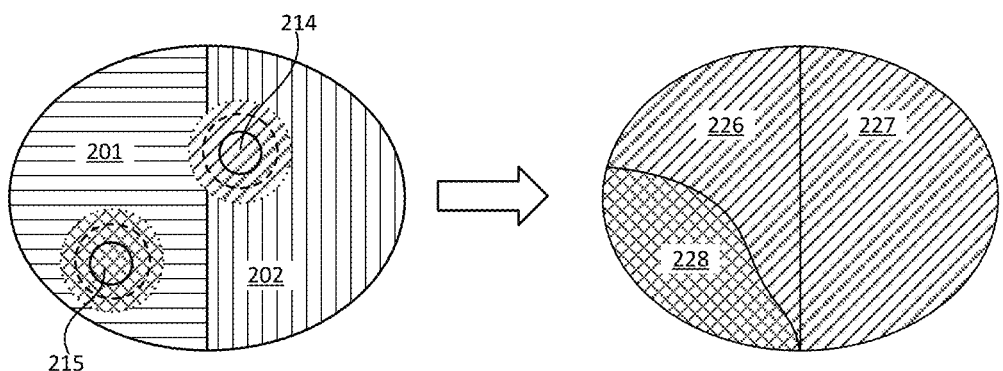

Similarly as for the examples described with reference to FIGS. 1B-1C, the relative locations of different seeds on the substrate may affect the extent to which the cluster is polyclonal, and the extent to which the cluster may be useable for SBS, and in particular for simultaneous paired-end reads. For example, as shown in FIG. 2C, a first seed 214 bridging substrate regions 201, 202 and a second seed 215 on substrate region 201 results in a polyclonal cluster within substrate region 201 that has a first region 226 resulting from amplification of seed 214 within substrate region 201, and a second region 228 resulting from amplification of seed 215 within substrate region 201; and a monoclonal cluster 227 within substrate region 202 resulting from amplification of seed 214 within substrate region 202. In the example of FIG. 2C, second region 228 is larger than second region 225 in FIG. 2B because seed 215 is more centrally located than is seed 213. In this example, substrate region 201 is polyclonal without being functionally monoclonal, while substrate region 202 is monoclonal. As such, regions 201 and 202 together may not be functionally monoclonal, and the extent to which the cluster is polyclonal may be too high for clusters 226, 228 to be useful for simultaneous paired-end reads. Additionally, because region 201 is not functionally monoclonal, region 201 may not be useful for sequencing, while region 202 may be used independently for sequencing.

Figure 2D:
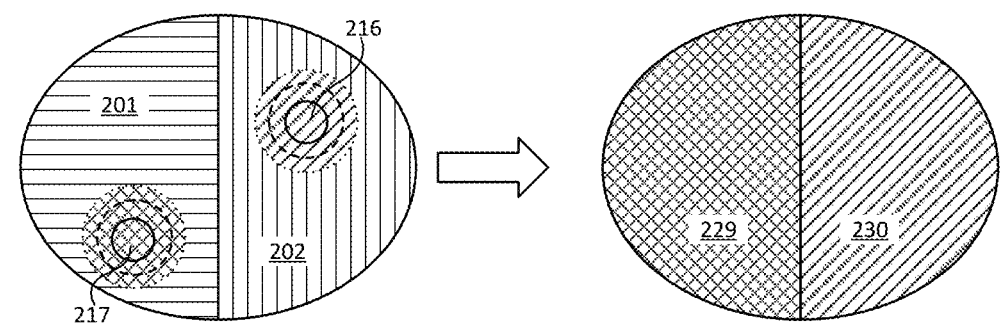

In another example, as shown in FIG. 2D, a first seed 216 on substrate region 202 and a second seed 217 on substrate region 201 results in a monoclonal cluster 229 within substrate region 201 resulting from amplification of seed 217 within substrate region 201, and a second monoclonal cluster within substrate region 202 resulting from amplification of seed 216 within substrate region 202. Although clusters 229, 230 are each monoclonal, they may not be useful for simultaneous paired-end reads because they have copies of different target polynucleotides than one another, and so may not be aligned with one another using software. Nonetheless, because each of clusters 229, 230 are monoclonal, or at least functionally monoclonal, those clusters may be used independently for sequencing although the sequences in the two clusters are not complementary to each other.

Examples provided herein may enhance the extent to which a cluster is monoclonal (including, but not limited to, on substrates with complex surfaces) through the use of modified primers, as compared to the monoclonality that may be achieved with the use of standard P5 and P7 primers. Such modified primers may include any suitable combination of one or more of modified sequence, modified length, use of non-nucleotide moieties, and use together with other modified primers. The modified primers may be used to reduce the effective amplification area, or otherwise bias the amplification, so as to enhance cluster monoclonality. For example, the number of seeds that may be expected to be amplified on a given region of the substrate in examples such as described with reference to FIGS. 1A-1C and 2A-2D may be expected to follow the Poisson distribution. In comparison, use of modified primers such as provided herein may provide monoclonality that exceeds that which would be predicted by the Poisson distribution.

First, some terms used herein will be briefly explained. Then, some example compositions and example methods for amplifying polynucleotides will be described.

Terms

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The terms "substantially," "approximately," and "about" used throughout this specification are used to describe and account for small fluctuations, such as due to variations in processing. For example, they may refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein, "hybridize" is intended to mean noncovalently associating a first polynucleotide to a second polynucleotide along the lengths of those polymers to form a double-stranded "duplex." For instance, two DNA polynucleotide strands may associate through complementary base pairing. The strength of the association between the first and second polynucleotides increases with the complementarity between the sequences of nucleotides within those polynucleotides. The strength of hybridization between polynucleotides may be characterized by a temperature of melting (Tm) at which 50% of the duplexes have polynucleotide strands that disassociate from one another. Polynucleotides that are "partially" hybridized to one another means that they have sequences that are complementary to one another, but such sequences are hybridized with one another along only a portion of their lengths to form a partial duplex. Polynucleotides with an "inability" to hybridize include those which are physically separated from one another such that an insufficient number of their bases may contact one another in a manner so as to hybridize with one another.

As used herein, the term "nucleotide" is intended to mean a molecule that includes a sugar and at least one phosphate group, and in some examples also includes a nucleobase. A nucleotide that lacks a nucleobase may be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

As used herein, the term "nucleotide" also is intended to encompass any nucleotide analogue which is a type of nucleotide that includes a modified nucleobase, sugar and/or phosphate moiety compared to naturally occurring nucleotides. Example modified nucleobases include inosine, xathanine, hypoxanthine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate. Nucleotides may include any suitable number of phosphates, e.g., three, four, five, six, or more than six phosphates.

As used herein, the term "polynucleotide" refers to a molecule that includes a sequence of nucleotides that are bonded to one another. A polynucleotide is one nonlimiting example of a polymer. Examples of polynucleotides include deoxyribonucleic acid (DNA), ribonucleic acid (RNA), and analogues thereof. A polynucleotide may be a single stranded sequence of nucleotides, such as RNA or single stranded DNA, a double stranded sequence of nucleotides, such as double stranded DNA, or may include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides may include non-naturally occurring DNA, such as enantiomeric DNA. The precise sequence of nucleotides in a polynucleotide may be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, a "polymerase" is intended to mean an enzyme having an active site that assembles polynucleotides by polymerizing nucleotides into polynucleotides. A polymerase can bind a primed single stranded target polynucleotide, and can sequentially add nucleotides to the growing primer to form a "complementary copy" polynucleotide having a sequence that is complementary to that of the target polynucleotide. Another polymerase, or the same polymerase, then can form a copy of the target nucleotide by forming a complementary copy of that complementary copy polynucleotide. Any of such copies may be referred to herein as "amplicons." DNA polymerases may bind to the target polynucleotide and then move down the target polynucleotide sequentially adding nucleotides to the free hydroxyl group at the 3' end of a growing polynucleotide strand (growing amplicon). DNA polymerases may synthesize complementary DNA molecules from DNA templates and RNA polymerases may synthesize RNA molecules from DNA templates (transcription). Polymerases may use a short RNA or DNA strand (primer), to begin strand growth. Some polymerases may displace the strand upstream of the site where they are adding bases to a chain. Such polymerases may be said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "primer" is defined as a polynucleotide to which nucleotides may be added via a free 3' OH group. A primer may include a 3' block preventing polymerization until the block is removed. A primer may include a modification at the 5' terminus to allow a coupling reaction or to couple the primer to another moiety. A primer may include one or more moieties which may be cleaved under suitable conditions, such as UV light, chemistry, enzyme, or the like. The primer length may be any suitable number of bases long and may include any suitable combination of natural and non-natural nucleotides. A target polynucleotide may include an "adapter" that hybridizes to (has a sequence that is complementary to) a primer, and may be amplified so as to generate a complementary copy polynucleotide by adding nucleotides to the free 3' OH group of the primer. A "capture primer" is intended to mean a primer that is coupled to the substrate and may hybridize to a second adapter of the target polynucleotide, while an "orthogonal capture primer" is intended to mean a primer that is coupled to the substrate and may hybridize to a first adapter of that target polynucleotide. The first adapter may have a sequence that is complementary to that of the orthogonal capture primer, and the second adapter may have a sequence that is complementary to that of the capture primer. A capture primer and an orthogonal capture primer may have different and independent sequences than one another. Additionally, a capture primer and an orthogonal capture primer may differ from one another in at least one other property. For example, the capture primer and the orthogonal capture primer may have different lengths than one another; either the capture primer or the orthogonal capture primer may include a non-nucleic acid moiety (such as a blocking group or excision moiety) that the other of the capture primer or the orthogonal capture primer lacks; or any suitable combination of such properties.

As used herein, the term "substrate" refers to a material used as a support for compositions described herein. Example substrate materials may include glass, silica, plastic, quartz, metal, metal oxide, organo-silicate (e.g., polyhedral organic silsesquioxanes (POSS)), polyacrylates, tantalum oxide, complementary metal oxide semiconductor (CMOS), or combinations thereof. An example of POSS can be that described in Kehagias et al., Microelectronic Engineering 86 (2009), pp. 776-778, which is incorporated by reference in its entirety. In some examples, substrates used in the present application include silica-based substrates, such as glass, fused silica, or other silica-containing material. In some examples, substrates may include silicon, silicon nitride, or silicone hydride. In some examples, substrates used in the present application include plastic materials or components such as polyethylene, polystyrene, poly(vinyl chloride), polypropylene, nylons, polyesters, polycarbonates, and poly(methyl methacrylate). Example plastics materials include poly(methyl methacrylate), polystyrene, and cyclic olefin polymer substrates. In some examples, the substrate is or includes a silica-based material or plastic material or a combination thereof. In particular examples, the substrate has at least one surface comprising glass or a silicon-based polymer. In some examples, the substrates may include a metal. In some such examples, the metal is gold. In some examples, the substrate has at least one surface comprising a metal oxide. In one example, the surface comprises a tantalum oxide or tin oxide. Acrylamides, enones, or acrylates may also be utilized as a substrate material or component. Other substrate materials may include, but are not limited to gallium arsenide, indium phosphide, aluminum, ceramics, polyimide, quartz, resins, polymers and copolymers. In some examples, the substrate and/or the substrate surface may be, or include, quartz. In some other examples, the substrate and/or the substrate surface may be, or include, semiconductor, such as GaAs or ITO. The foregoing lists are intended to be illustrative of, but not limiting to the present application. Substrates may comprise a single material or a plurality of different materials. Substrates may be composites or laminates. In some examples, the substrate comprises an organo-silicate material. Substrates may be flat, round, spherical, rod-shaped, or any other suitable shape. Substrates may be rigid or flexible. In some examples, a substrate is a bead or a flow cell.

In some examples, a substrate includes a patterned surface. A "patterned surface" refers to an arrangement of different regions in or on an exposed layer of a substrate. For example, one or more of the regions may be features where one or more capture primers are present. The features can be separated by interstitial regions where capture primers are not present. In some examples, the pattern may be an x-y format of features that are in rows and columns. In some examples, the pattern may be a repeating arrangement of features and/or interstitial regions. In some examples, the pattern may be a random arrangement of features and/or interstitial regions. In some examples, substrate includes an array of wells (depressions) in a surface. The wells may be provided by substantially vertical sidewalls. Wells may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface of a substrate may include wells in an array of wells (e.g., microwells or nanowells) on glass, silicon, plastic or other suitable material(s) with a patterned, covalently-linked gel such as poly (N-(5-azidoacetamidylpentyl) acrylamide-co-acrylamide) (PAZAM). The process creates gel pads used for sequencing that may be stable over sequencing runs with a large number of cycles. The covalent linking of the polymer to the wells may be helpful for maintaining the gel in the structured features throughout the lifetime of the structured substrate during a variety of uses. However in many examples, the gel need not be covalently linked to the wells. For example, in some conditions silane free acrylamide (SFA), which is not covalently attached to any part of the structured substrate, may be used as the gel material.

In particular examples, a structured substrate may be made by patterning a suitable material with wells (e.g. microwells or nanowells), coating the patterned material with a gel material (e.g., PAZAM, SFA or chemically modified variants thereof, such as the azidolyzed version of SFA (azido-SFA)) and polishing the surface of the gel coated material, for example via chemical or mechanical polishing, thereby retaining gel in the wells but removing or inactivating substantially all of the gel from the interstitial regions on the surface of the structured substrate between the wells. Primers may be attached to gel material. A solution including a plurality of target polynucleotides (e.g., a fragmented human genome or portion thereof) may then be contacted with the polished substrate such that individual target polynucleotides will seed individual wells via interactions with primers attached to the gel material; however, the target polynucleotides will not occupy the interstitial regions due to absence or inactivity of the gel material. Amplification of the target polynucleotides may be confined to the wells because absence or inactivity of gel in the interstitial regions may inhibit outward migration of the growing cluster. The process is conveniently manufacturable, being scalable and utilizing conventional micro- or nano-fabrication methods.

A patterned substrate may include, for example, wells etched into a slide or chip. The pattern of the etchings and geometry of the wells may take on a variety of different shapes and sizes, and such features may be physically or functionally separable from each other. Particularly useful substrates having such structural features include patterned substrates that may select the size of solid particles such as microspheres. An exemplary patterned substrate having these characteristics is the etched substrate used in connection with BEAD ARRAY technology (Illumina, Inc., San Diego, Calif.).

In some examples, a substrate described herein forms at least part of a flow cell or is located in or coupled to a flow cell. Flow cells may include a flow chamber that is divided into a plurality of lanes or a plurality of sectors. Example flow cells and substrates for manufacture of flow cells that may be used in methods and compositions set forth herein include, but are not limited to, those commercially available from Illumina, Inc. (San Diego, CA).

As used herein, the term "directly" when used in reference to a layer covering the surface of a substrate is intended to mean that the layer covers the substrate's surface without a significant intermediate layer, such as, e.g., an adhesive layer or a polymer layer. Layers directly covering a surface may be attached to this surface through any chemical or physical interaction, including covalent bonds or non-covalent adhesion.

As used herein, the term "immobilized" when used in reference to a polynucleotide is intended to mean direct or indirect attachment to a substrate via covalent or non-covalent bond(s). In certain examples, covalent attachment may be used, or any other suitable attachment in which the polynucleotides remain stationary or attached to a substrate under conditions in which it is intended to use the substrate, for example, in polynucleotide amplification or sequencing. Polynucleotides to be used as capture primers or as target polynucleotides may be immobilized such that a 3'-end is available for enzymatic extension and at least a portion of the sequence is capable of hybridizing to a complementary sequence. Immobilization may occur via hybridization to a surface attached oligonucleotide, in which case the immobilized oligonucleotide or polynucleotide may be in the 3'-5' orientation. Alternatively, immobilization may occur by means other than base-pairing hybridization, such as covalent attachment.

As used herein, the term "array" refers to a population of substrate regions that may be differentiated from each other according to relative location. Different molecules (such as polynucleotides) that are at different regions of an array may be differentiated from each other according to the locations of the regions in the array. An individual region of an array may include one or more molecules of a particular type. For example, a substrate region may include a single target polynucleotide having a particular sequence, or a substrate region may include several polynucleotides having the same sequence (or complementary sequences thereof). The regions of an array respectively may include different features than one another on the same substrate. Exemplary features include without limitation, wells in a substrate, beads (or other particles) in or on a substrate, projections from a substrate, ridges on a substrate or channels in a substrate. The regions of an array respectively may include different regions on different substrates than each other. Different molecules attached to separate substrates may be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "plurality" is intended to mean a population of two or more different members. Pluralities may range in size from small, medium, large, to very large. The size of small plurality may range, for example, from a few members to tens of members. Medium sized pluralities may range, for example, from tens of members to about 100 members or hundreds of members. Large pluralities may range, for example, from about hundreds of members to about 1000 members, to thousands of members and up to tens of thousands of members. Very large pluralities may range, for example, from tens of thousands of members to about hundreds of thousands, a million, millions, tens of millions and up to or greater than hundreds of millions of members. Therefore, a plurality may range in size from two to well over one hundred million members as well as all sizes, as measured by the number of members, in between and greater than the above exemplary ranges. Exemplary polynucleotide pluralities include, for example, populations of about $1\times10^5$ or more, $5\times10^5$ or more, or $1\times10^6$ or more different polynucleotides. Accordingly, the definition of the term is intended to include all integer values greater than two. An upper limit of a plurality may be set, for example, by the theoretical diversity of polynucleotide sequences in a sample.

As used herein, the term "double-stranded," when used in reference to a polynucleotide, is intended to mean that all or substantially all of the nucleotides in the polynucleotide are hydrogen bonded to respective nucleotides in a complementary polynucleotide. A "partially" double stranded polynucleotide may have at least about 10%, at least about 25%, at least about 50%, at least about 60%, at least about 70%, at least about 80%, at least about 90% or at least about 95% of its nucleotides, but fewer than all of its nucleotides, hydrogen bonded to nucleotides in a complementary polynucleotide.

As used herein, the term "single-stranded," when used in reference to a polynucleotide, means that essentially none of the nucleotides in the polynucleotide are hydrogen bonded to a respective nucleotide in a complementary polynucleotide. A polynucleotide that has an "inability" to hybridize to another polynucleotide may be single-stranded.

As used herein, the term "target polynucleotide" is intended to mean a polynucleotide that is the object of an analysis or action. The analysis or action includes subjecting the polynucleotide to amplification, sequencing and/or other procedure. A target polynucleotide may include nucleotide sequences additional to a target sequence to be analyzed. For example, a target polynucleotide may include one or more adapters, including an adapter that functions as a primer binding site, that flank(s) a target polynucleotide sequence that is to be analyzed. A target polynucleotide hybridized to a capture primer may include nucleotides that extend beyond the 5' or 3' end of the capture oligonucleotide in such a way that not all of the target polynucleotide is amenable to extension. In particular examples, target polynucleotides may have different sequences than one another but may have first and second adapters that are the same as one another. The two adapters that may flank a particular target polynucleotide sequence may have the same sequence as one another, or complementary sequences to one another, or the two adapters may have different sequences. Thus, species in a plurality of target polynucleotides may include regions of known sequence that flank regions of unknown sequence that are to be evaluated by, for example, sequencing (e.g., SBS). In some examples, target polynucleotides carry an adapter at a single end, and such adapter may be located at either the 3' end or the 5' end the target polynucleotide. Target polynucleotides may be used without any adapter, in which case a primer binding sequence may come directly from a sequence found in the target polynucleotide.

The terms "polynucleotide" and "oligonucleotide" are used interchangeably herein. The different terms are not intended to denote any particular difference in size, sequence, or other property unless specifically indicated otherwise. For clarity of description the terms may be used to distinguish one species of polynucleotide from another when describing a particular method or composition that includes several polynucleotide species.

As used herein, the term "amplicon," when used in reference to a polynucleotide, is intended to means a product of copying the polynucleotide, wherein the product has a nucleotide sequence that is substantially the same as, or is substantially complementary to, at least a portion of the nucleotide sequence of the polynucleotide. "Amplification" and "amplifying" refer to the process of making an amplicon of a polynucleotide. A first amplicon of a target polynucleotide may be a complementary copy. Additional amplicons are copies that are created, after generation of the first amplicon, from the target polynucleotide or from the first amplicon. A subsequent amplicon may have a sequence that is substantially complementary to the target polynucleotide or is substantially identical to the target polynucleotide. It will be understood that a small number of mutations (e.g., due to amplification artifacts) of a polynucleotide may occur when generating an amplicon of that polynucleotide.

A substrate region that includes substantially only amplicons of a given polynucleotide may be referred to as "monoclonal," while a substrate region that includes amplicons of polynucleotides having different sequences than one another may be referred to as "polyclonal." A substrate region that includes a sufficient number of amplicons of a given polynucleotide to be used to sequence that polynucleotide maybe referred to as "functionally monoclonal." Illustratively a substrate region in which about 60% or greater of the amplicons are of a given polynucleotide may be considered to be "functionally monoclonal." Additionally, or alternatively, a substrate region from which about 60% or more of a signal is from amplicons of a given polynucleotide may be considered to be "functionally monoclonal." A polyclonal region of a substrate may include different sub-regions therein that respectively are monoclonal. Each such monoclonal region, whether within a larger polyclonal region or on its own, may correspond to a "cluster" generated from a "seed." The "seed" may refer to a single target polynucleotide, while the "cluster" may refer to a collection of amplicons of that target polynucleotide.

Compositions and Methods for Amplifying Polynucleotides

Examples provided herein relate to generating clusters that are substantially monoclonal, by providing capture primers with selected characteristics in the substrate region(s) in which the clusters are to be generated. The examples herein are particularly well suited to generating clusters for use in simultaneous paired-end reads in which an amplified polynucleotide's sequence is read using SBS in a first substrate region, and that polynucleotide's complementary sequence is read using SBS in a second substrate, in parallel with one another, but it should be understood that the examples are generally applicable to any type of cluster.

In some examples, although seeding with various polynucleotides may occur anywhere on first and second substrate regions in accordance with the Poisson distribution, capture primers coupled to the substrate in the first and second regions may be selected such that a target polynucleotide that is captured sufficiently near to the border between those regions is preferentially amplified as compared to polynucleotides that are captured further from the border. Such preferential amplification may be achieved, in some examples, by shortening a subset of the capture primers (e.g., P5*primers) in the first region as compared to other capture primers (e.g., full length P7 primers) in the first region, shortening a subset of other capture primers (e.g., P7*primers) in the second region as compared to other capture primers (e.g., full length P5 primers), and providing target polynucleotides which have short adapters (e.g., shortened versions of cP5 and cP7). As explained in greater detail below, these various shortened capture primers and shortened adapters may bias amplification for certain target polynucleotides that may become coupled to the substrate. For example, a target polynucleotide that forms a seed at the border between the first and second regions may be amplified more readily than polynucleotides that form seeds sufficiently far from the border. The resulting amplicon, as compared to the target polynucleotide, may be extended so as to include full length adapters (e.g., full length cP5 and cP7 adapters), thus facilitating subsequent amplification of that amplicon throughout both the first and second regions of the substrate.

Figure 3A:
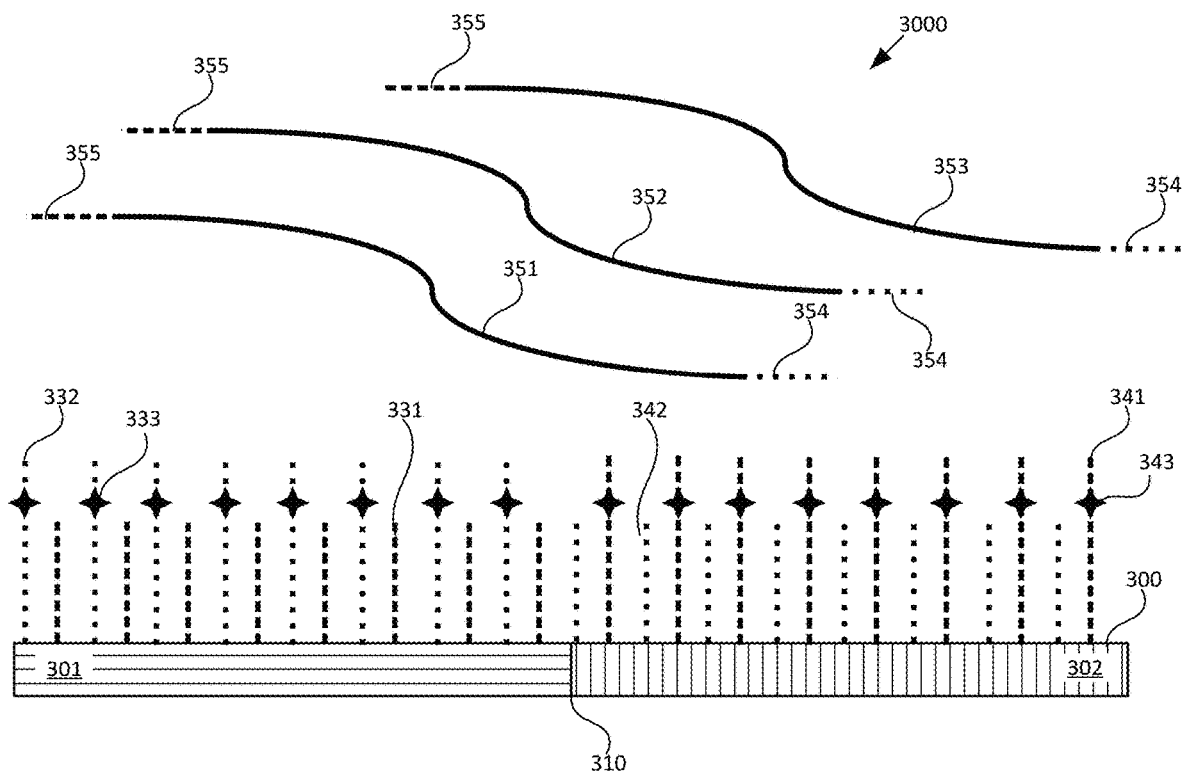
FIGS. 3A-3J schematically illustrate example compositions and operations in a process flow for amplifying a polynucleotide using primers of different lengths in first and second substrate regions.

For example, FIGS. 3A-3J schematically illustrate example compositions and operations in a process flow for amplifying a polynucleotide using primers of different lengths in first and second substrate regions. Referring first to FIG. 3A, composition 3000 includes substrate 300 and a plurality of primers coupled thereto. In this example, substrate 300 includes first region 301 and second region 302, which may be adjacent to one another. Optionally, first region 301 and second region 302 may have different surface treatments than one another, e.g., different polymers than one another, or the same polymer as one another but with different moieties attached thereto, to which the different capture primers selectively may be coupled. As explained below, primers respectively coupled to first and second regions 301, 302 may include capture primers that differ from one another in at least one characteristic, and orthogonal capture primers that differ from one another in at least one characteristic, so as to inhibit amplification of target polynucleotides that hybridize to such capture primers or orthogonal capture primers at regions sufficiently far from border 310 between the first and second regions.

For example, first plurality of capture primers 331 may be coupled to the first region 301 of substrate 300, and second plurality of capture primers 341 may be coupled to the second region 302 of substrate 300. The capture primers 341 of the second plurality of capture primers may be longer than the capture primers 331 of the first plurality of capture primers. First plurality of orthogonal capture primers 332 may be coupled to first region 301 of substrate 300, and second plurality of orthogonal capture primers 342 may be coupled to second region 302 of the substrate. The orthogonal capture primers 342 of the second plurality of orthogonal capture primers may be shorter than the orthogonal capture primers 332 of the first plurality of orthogonal capture primers.

Illustratively, the capture primers 331 of the first plurality of capture primers may be, in some examples, at least 2 bases shorter than the capture primers 341 of the second plurality of capture primers, e.g., may be at least 3 bases shorter, at least 4 bases shorter, at least 5 bases shorter, at least 6 bases shorter, at least 7 bases shorter, at least 8 bases shorter, at least 9 bases shorter, or at least 10 bases shorter, than the capture primers 341 of the second plurality of capture primers. The orthogonal capture primers 342 of the second plurality of orthogonal capture primers may be, in some examples, at least 2 bases shorter than the capture primers 341 of the second plurality of capture primers, e.g., may be at least 3 bases shorter, at least 4 bases shorter, at least 5 bases shorter, at least 6 bases shorter, at least 7 bases shorter, at least 8 bases shorter, at least 9 bases shorter, or at least 10 bases shorter than the orthogonal capture primers 332 of the first plurality of orthogonal capture primers.

Not all primers coupled to substrate 300 need to be different lengths than one another. For example, the capture primers 331 of the first plurality of capture primers may be, in some examples, approximately the same length as the orthogonal capture primers 342 of the second plurality of capture primers. The capture primers 341 of the second plurality of capture primers may be, in some examples, approximately the same length as the orthogonal capture primers 332 of the first plurality of capture primers. However, it should be appreciated that any suitable respective lengths of capture primers and orthogonal capture primers may be used in suitable regions of substrate 300. As described in greater detail below, the different lengths of capture primers 331, 341 than one another in the first and second regions, and the different lengths of the capture primers 332, 342 than one another in the first and second regions, may cause a target polynucleotide that lands sufficiently near border 310 between the first and second regions to be preferentially amplified as compared to target polynucleotides that land sufficiently far from border 310. Then, that amplicon may be further preferentially amplified throughout the first and second regions as compared to target polynucleotides that land sufficiently far from border 310, as described in greater detail below.

As shown in FIG. 3A, composition 3000 further may include a fluid that includes target polynucleotides 351, 352, 353, e.g., polynucleotides that are to be amplified and eventually sequenced. Each of the target polynucleotides 351, 352, 353 may include first adapter 354 that is complementary to the orthogonal capture primers 332, 342 of the first and second pluralities of orthogonal capture primers, and a second adapter 355 that is complementary to the capture primers 331, 341 of the first and second pluralities of capture primers. The first adapters 354 of target polynucleotides 351, 352, 353 may be shorter than orthogonal capture primers 332 of the first plurality of orthogonal capture primers, in some examples, at least 2 bases shorter than the orthogonal capture primers 332, e.g., may be at least 3 bases shorter, at least 4 bases shorter, at least 5 bases shorter, at least 6 bases shorter, at least 7 bases shorter, at least 8 bases shorter, at least 9 bases shorter, or at least 10 bases shorter than the orthogonal capture primers 332. The second adapters 355 of target polynucleotides 351, 352, 353 may be shorter than capture primers 341 of the second plurality of capture primers, in some examples, at least 2 bases shorter than the capture primers 341, e.g., may be at least 3 bases shorter, at least 4 bases shorter, at least 5 bases shorter, at least 6 bases shorter, at least 7 bases shorter, at least 8 bases shorter, at least 9 bases shorter, or at least 10 bases shorter than the capture primers 341. The first and second adapters 354, 355 may be, but need not necessarily be, the same length as one another.

In one nonlimiting example, the capture primers 341 of the second plurality of capture primers are P5 capture primers, and the orthogonal capture primers 332 of the first plurality of orthogonal capture primers are P7 capture primers. P5 capture primers, which are commercially available from Illumina, Inc. (San Diego, CA) have the sequence 5'-AATGATACGGCGACCACCGA-3' ((SEQ ID NO: 1)). P7 capture primers, which also are commercially available from Illumina, Inc., have the sequence 5'-CAAGCAGAA-GACGGCATACGA-3' (SEQ ID NO: 2). In some examples, the capture primers 331 of the first plurality of capture primers are shortened P5 capture primers (which may be designated P5* herein), and the orthogonal capture primers of the second plurality of orthogonal capture primers are shortened P7 capture primers (which may be designated P7*) herein. For example, the above-given sequences for P5 and P7 may be shortened from the 3'-end by between about 2 to 10 bases to form the shortened P5 capture primers (P5*) and shortened P7 capture primers (P7*), respectively. In some examples, the shortened P7 capture primers (P7*) may have the sequence 5'-TTTTTTCAAGCAGAAGACGGC-3' (SEQ ID NO: 3). In some examples, the shortened P5 capture primers (P5*) may have the sequence 5'-TTTT-TAATGATACGGCGACCA-3' (SEQ ID NO: 4).

Second adapters 355 may be shortened complementary P5 adapters (which may be designated cP5* herein), e.g., may be shortened versions of the full-length complementary P5 adapters (which may be designated cP5 herein). The full-length complementary P5 adapters (cP5) may have the sequence 5'-TCGGTGGTCGCCGTATCATT-3' (SEQ ID NO: 5), and are commercially available from Illumina, Inc. The shortened complementary P5 adapters (cP5*) may have the sequence 3'-GCGACCACCGAGATCTACAC-5' (SEQ ID NO: 6). First adapters 354 may be shortened complementary P7 adapters (which may be designated cP7* herein), e.g., may be shortened versions of the full-length complementary P7 adapters (which may be designated cP7 herein). The full-length complementary P7 adapters (cP7) may have the sequence 5'-TCGTATGCCGTCTTCTGCTTG-3' (SEQ ID NO: 7), and are commercially available from Illumina, Inc. The shortened complementary P7 adapters (cP7*) may have the sequence 3'-GACGGCATACGAGAT-5' (SEQ ID NO: 8), where the G indicated in bold may, in some examples, be 8-oxo-G which may be a cleavable moiety such as described elsewhere herein. Illustratively, the above-sequences for cP5 and cP7 may be shortened from either the 3'-end or the 5'-end, or from both the 3'-end and the 5'-end, by about 2 to 10 bases to form the shortened cP7 adapters (cP7*) and shortened cP5 adapters (cP5*).

Figure 3B:
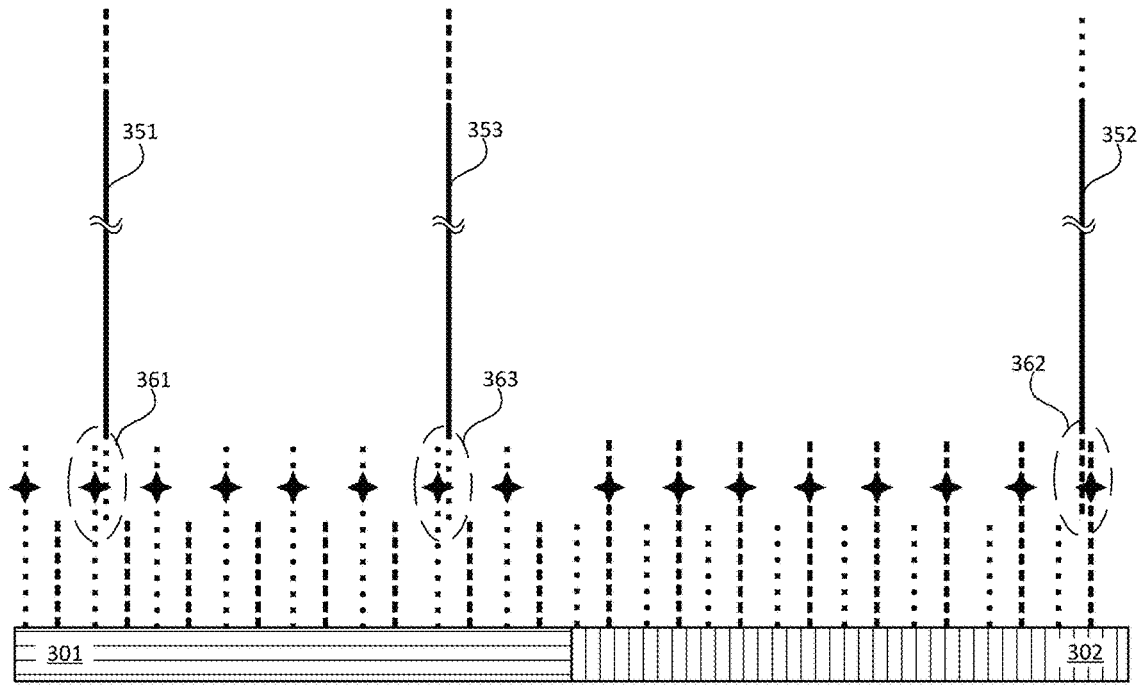

As illustrated in FIG. 3B, adapters 354, 355 of first, second, and third target polynucleotides 351, 352, 353 may randomly hybridize to different capture primers in different locations of substrate 300, e.g., in accordance with the Poisson distribution. In the particularly illustrated example, first adapter 354 of target polynucleotide 351 hybridizes to an orthogonal capture primer 332 of the first plurality of orthogonal capture primers in first region 301 of substrate 300 to form duplex 361. Second adapter 355 of target polynucleotide 352 hybridizes to a capture primer 341 of the second plurality of capture primers in second region 302 of substrate 300 to form duplex 362. First adapter 354 of target polynucleotide 353 hybridizes to an orthogonal capture primer 332 of the first plurality of orthogonal capture primers in first region 301 of substrate 300 to form duplex 363. The duplexes resulting from such initial hybridizations between adapters and capture primers or orthogonal capture primers may have melting temperatures (Tm) of greater than about 40° C., e.g., of greater than about 45° C., or of greater than about 50° C., or of greater than about 55° C., or of greater than about 60° C., or of greater than about 65° C., or of greater than about 70° C., e.g., may be relatively stable at the reaction temperature or other temperature at which composition 3000 is held. However, as described herein, the particular locations on the substrate at which the target polynucleotides' adapters initially hybridize to capture primers or orthogonal capture primers affect the extent to which such polynucleotides being amplified. For example, target polynucleotides that initially hybridize sufficiently near border 310 between first and second substrate regions 301, 302 may be readily amplified as compared to polynucleotides that initially hybridize sufficiently far from that border.

Figure 3C:
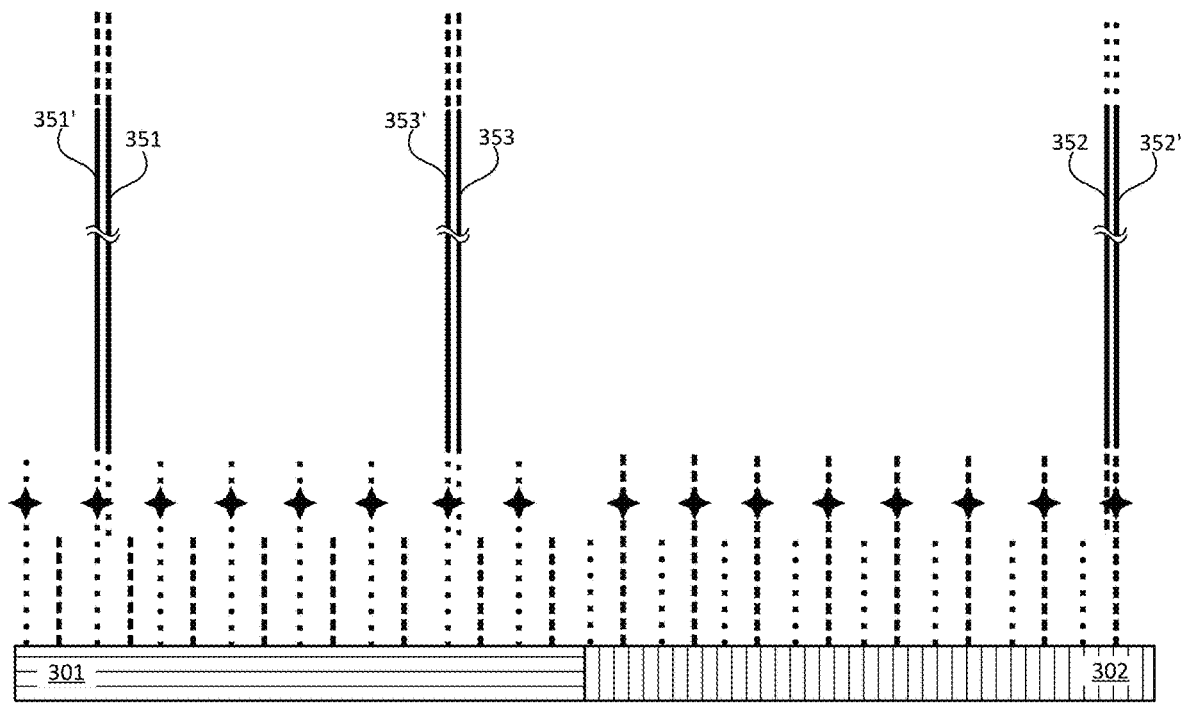
Figure 3D:
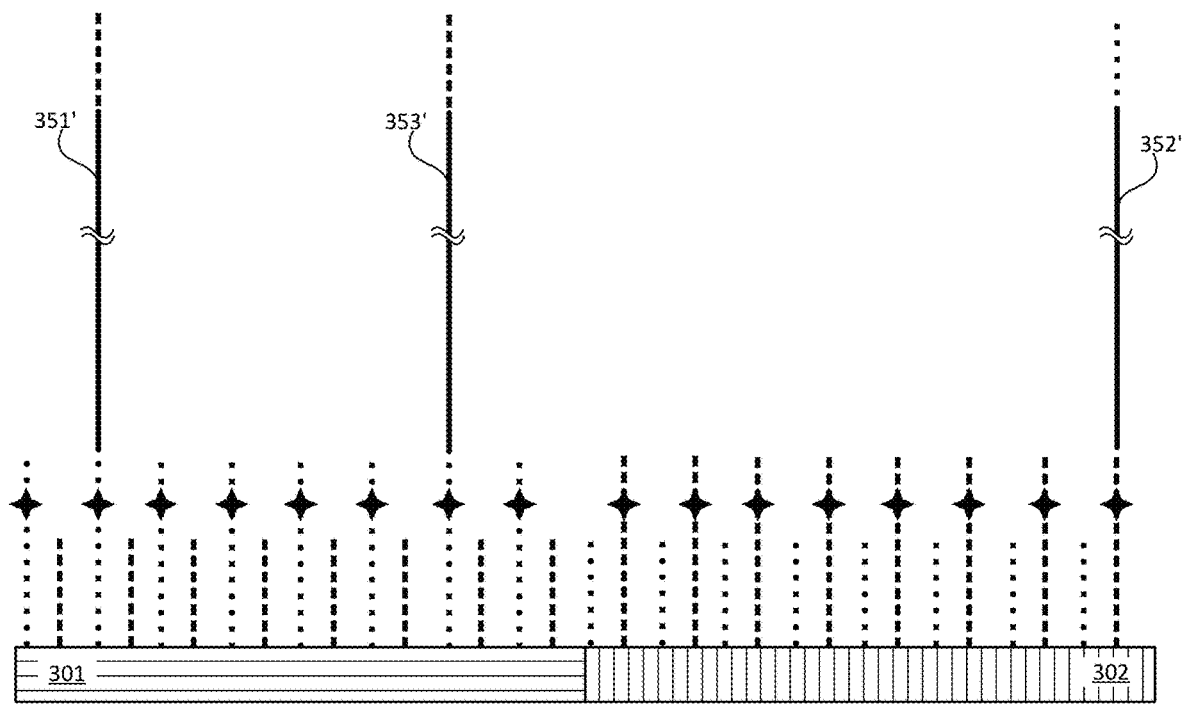

For example, as illustrated in FIG. 3C, after the initial hybridizations described with reference to FIG. 3B, each of first, second, and third target polynucleotides 351, 352, 353 may be amplified, e.g., forming first amplicon 351', second amplicon 352', and third amplicon 353' respectively. Following such amplification, the first, second, and third target polynucleotides 351, 352, 353 may be dehybridized in a manner such as illustrated in FIG. 3D, while first, second, and third amplicons 351', 352', 353' remain covalently bound to substrate 300. Note that such dehybridization need not necessarily be performed. For example, instead of dehybridizing the first, second, and third target polynucleotides 351, 352, 353, such polynucleotides may remain hybridized to the substrate and may be further amplified using a strand invasion process such as known in the art and may be referred to as ExAmp.

Figure 3E:
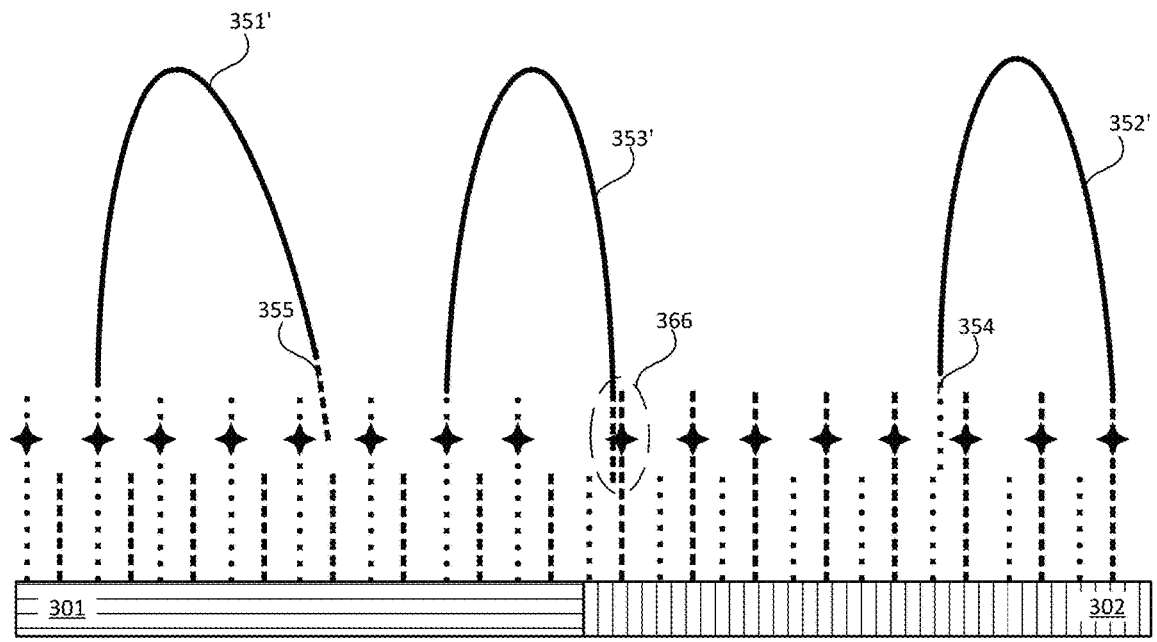

As illustrated in FIG. 3E, after the initial amplifications described with reference to FIGS. 3C-3D, the resulting amplicons may bend so as potentially to hybridize to other capture primers or orthogonal capture primers on substrate 300. For example, first adapter 354 of second amplicon 352' may insufficiently hybridize to a second one of the orthogonal capture primers 342 so as to be stable at the reaction temperature. For example, because each of the orthogonal capture primers 342 is relatively short, and first adapter 354 of second amplicon 352' is relatively short, second amplicon 352' may be unable to bend sufficiently far to sufficiently align the sequence of any of the orthogonal capture primers 342 with the sequence of adapter 354. As such, any duplex formed between first adapter 354 of second amplicon and any orthogonal capture primer 342 may have a melting temperature ($T_m$) that is below the reaction temperature, and any such duplex thus may melt sufficiently rapidly as to inhibit amplification of second amplicon 352'. For example, any duplex 365 resulting from at most partial hybridization between the first adapter 354 of second amplicon 352' and any of the orthogonal capture primers 342 may have a melting temperature (Tm) of less than about 20° C., e.g., of less than about 15° C., of less than about 10° C., or of less than about 5° C. Illustratively, using the example sequences provided above, a shortened P7 capture primer (P7*) may overlap a shortened complementary P7 adapter (cP7*) by only about 5 bases or fewer, and a shortened P5 capture primer (P5*) may overlap a shortened complementary P5 primer by only about 10 bases or fewer, or about 9 bases or fewer, or about 8 bases or fewer, or about 7 bases or fewer, or about 6 bases or fewer, or about 5 bases or fewer, or about 4 bases or fewer, or about 3 bases or fewer, or about 2 bases or fewer, or about 1 base, or no bases. As such, at the reaction temperature, any such duplex is unlikely to be formed for a sufficient amount of time for a polymerase (not specifically illustrated) to begin to form an amplicon of second amplicon 352' using any orthogonal capture primer 342 as a primer for such amplification. Similarly, second adapter 355 of first amplicon 351' may be unable to sufficiently hybridize to any of the capture primers 331 of the first plurality of capture primers. For example, because each of capture primers 331 is relatively short, and adapter 355 is relatively short, first amplicon 351' may be unable to bend sufficiently far as to bring the sequence of adapter 355 into sufficient contact with the sequence of any of the capture primers 331. Such inability to sufficiently hybridize may inhibit amplification of first amplicon 351', e.g., may inhibit a polymerase (not specifically illustrated) from being able to form an amplicon of first amplicon 351' using any capture primer 331 as a primer for such amplification.

In comparison, third amplicon 353' is sufficiently close to border 310 between the first and second regions 301, 302 of substrate 300 that second adapter 355 of that amplicon may cross the border so as to completely hybridize to a capture primer 341 of the second plurality of capture primers in second region 302 of substrate 300 to form duplex 366. For example, because capture primer 341 is full length, even though adapter 355 is relatively short, third amplicon 353' may be able to bend sufficiently far as to align the sequence of adapter 355 with the sequence of the capture primer 341. The hybridization of the second adapter 355 of third amplicon 353' to capture primer 341 may promote amplification of third amplicon 353', and thus promote further amplification of target polynucleotide 353.

For example, duplex 366 resulting from hybridization between adapter 355 of third amplicon 353' and capture primer 341 may have a melting temperature (Tm) of greater than about 40° C., e.g., of greater than about 45° C., or of greater than about 50° C., or of greater than about 55° C., or of greater than about 60° C., or of greater than about 65° C., or of greater than about 70° C. As such, at the reaction temperature, duplex 366 (as well as duplex 363 described with reference to FIG. 3B) is likely to be formed for a sufficient amount of time for a polymerase (not specifically illustrated) to begin to form an amplicon of third amplicon 353' using capture primer 341 as a primer for such amplification.

As such, a target polynucleotide (or amplicon thereof) that may be considered to be "sufficiently near the border" may hybridize to a capture primer on one side of border 310, and may hybridize to an orthogonal capture primer on the other side of border 310. It will be appreciated that the longer the target polynucleotide (or amplicon), the further from the border it may be able to hybridize to a capture primer on one side of border 310 and to an orthogonal capture primer on the other side of border 310. Illustratively, a target polynucleotide (or amplicon) with a length of 500 bases may be approximately 150 nm long. As such, depending on where that target polynucleotide (or amplicon) initially hybridizes, up to about 150 nm on either side of border 310 may be "sufficiently near the border" for that polynucleotide. Conversely, a target polynucleotide (or amplicon) with a length of 250 bases may be approximately 75 nm long, while a target polynucleotide (or amplicon) with a length of 1000 bases may be approximately 300 nm long. In any such examples, the distance across border 310 that the target polynucleotide (or amplicon) may reach, and thus be preferentially amplified, relates to the physical length of that target polynucleotide (or amplicon).

Figure 3F:
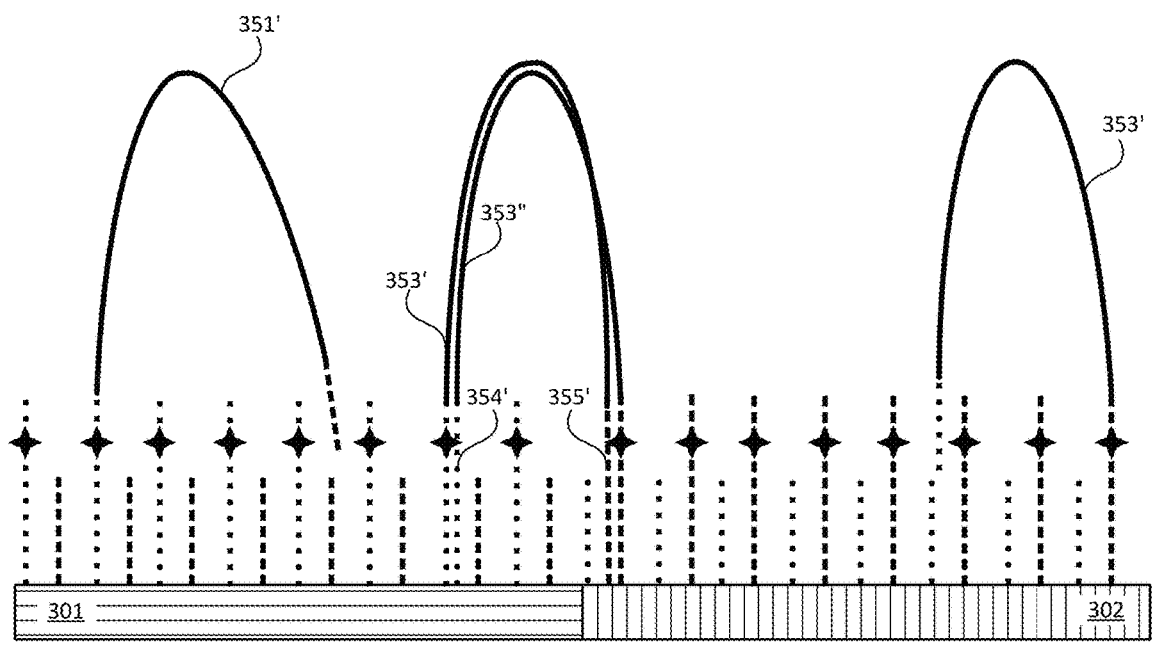
Figure 3G:
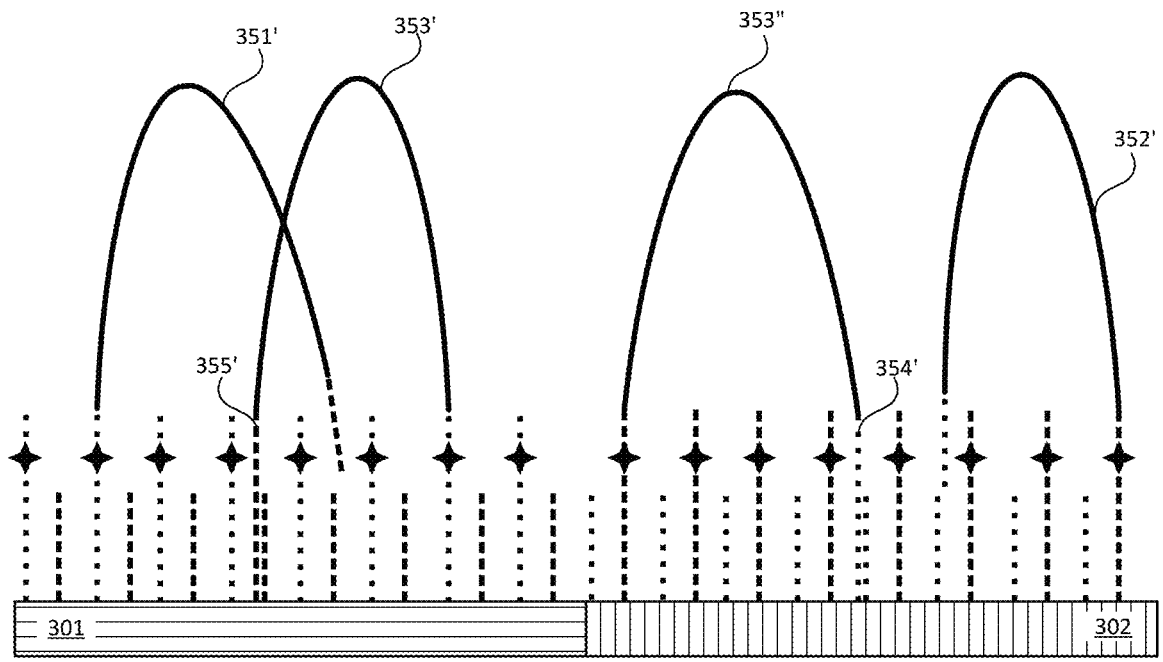
Figure 3H:
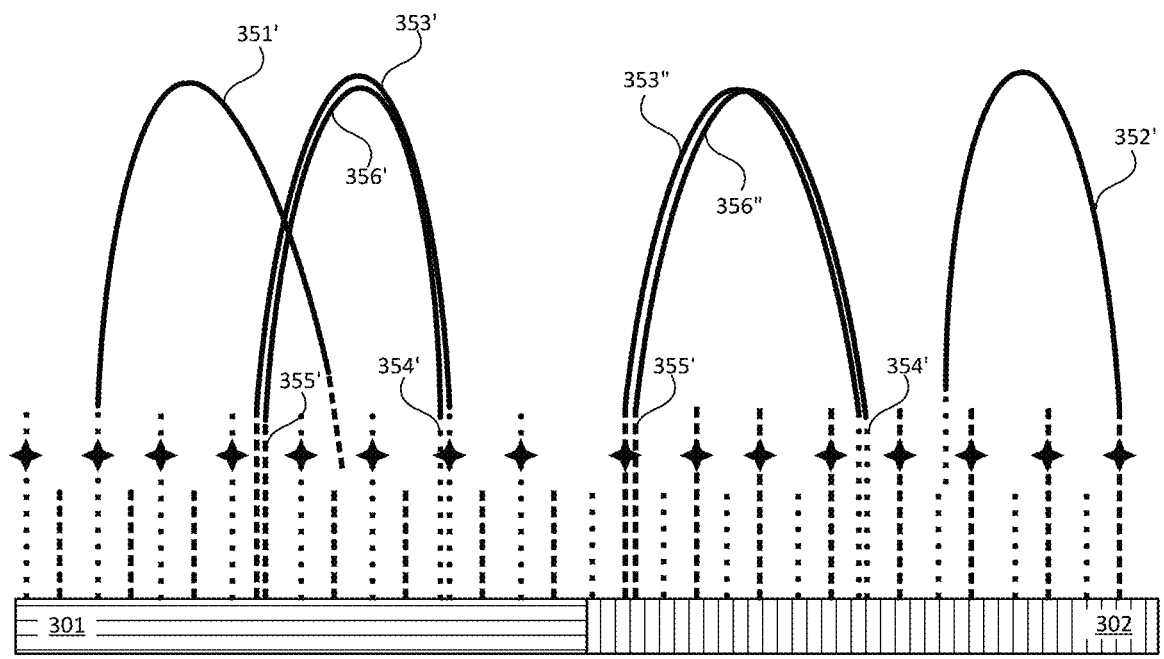
Figure 3I:
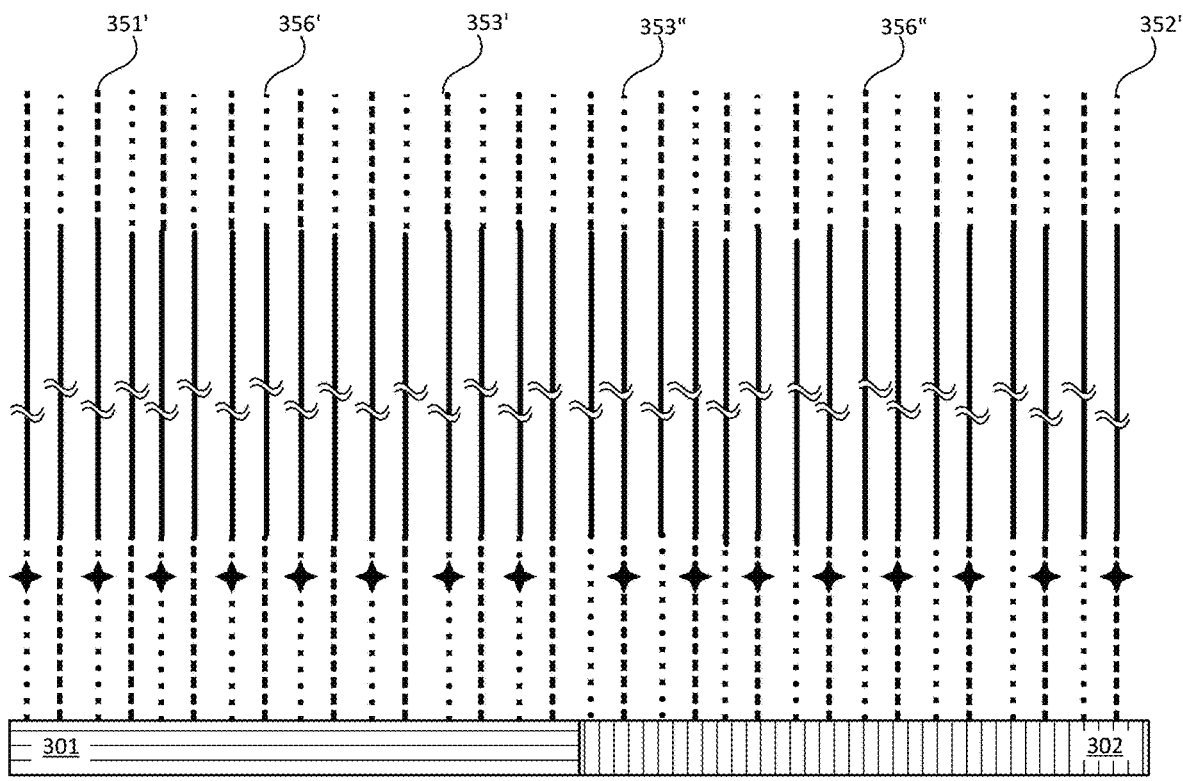

FIG. 3F illustrates the composition of FIG. 3E following another amplification operation. It may be seen that the composition includes an additional amplicon 353" of amplicon 353'. Such additional amplicon may be hybridized to amplicon 353'. As shown in FIG. 3F, the amplification operation may extend the first and second adapters 354, 355 of additional amplicon 353" to form extended (e.g., full length) adapters 354', 355' using the sequences of the first orthogonal capture primer 332 and the second capture primer 341, respectively. In comparison, the composition may not include any further amplicons of amplicons 351', 352', e.g., because insufficient hybridization of those amplicons' adapters to capture primers or orthogonal capture primers may inhibit any amplification of those amplicons. The amplification operation may be repeated any suitable number of times so as to generate further amplicons of amplicons 353', 353", the full length adapters 354', 355' of each of which may readily hybridize with respective shortened capture primers 331, 342 or with full length capture primers 332, 341 as appropriate. For example, as shown in FIG. 3G, a full length first adapter 354' of amplicon 353' may hybridize with an orthogonal capture primer 332 of the first plurality of capture primers in first region 301, and a full length second adapter 355' of amplicon 353" may hybridize with a capture primer 341 of the second plurality of capture primers in second region 302. As shown in FIG. 3H, following another amplification operation, additional amplicons 356', 356" of target polynucleotide 353 then may be formed. If amplification operations are repeated until first and second substrate regions 401, 402 are full, both adapters of the resulting amplicons may not necessarily be hybridized to corresponding capture primers or orthogonal capture primers, and as such the amplicons may extend linearly away from the substrate as illustrated in FIG. 3I.

Figure 3J:
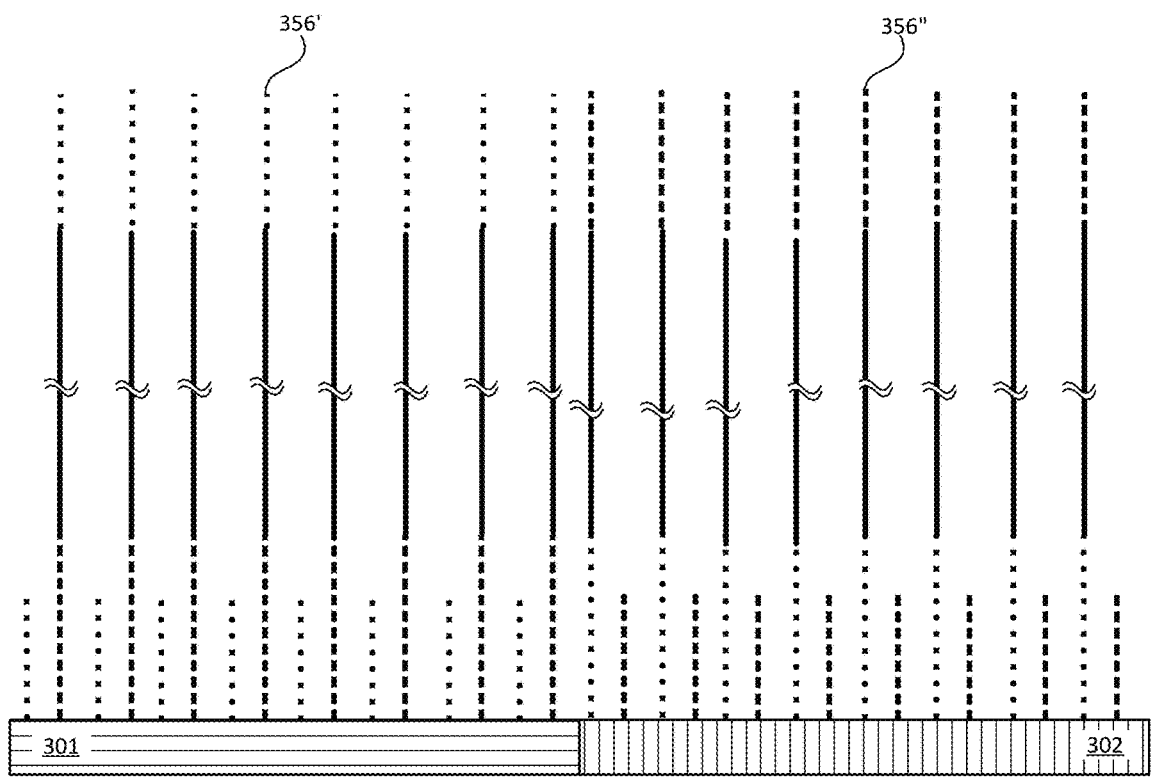

Amplification operations may be formed any suitable number of times so as to substantially fill both of the first and second substrate regions 301, 302 with at least functionally monoclonal clusters, and in some examples substantially monoclonal clusters, e.g., with amplicons of target polynucleotide 353. For example, amplicons within each of first and second substrate regions 301, 302 each may include at least about 60% amplicons of one selected target polynucleotide, or at least about 70% amplicons of one selected target polynucleotide, or at least about 80% amplicons of one selected target polynucleotide, or at least about 90% amplicons of one selected target polynucleotide, or at least about 95% amplicons of one selected target polynucleotide, or at least about 98% amplicons of one selected target polynucleotide, or at least about 99% amplicons of one selected target polynucleotide, or about 100% amplicons of one selected target polynucleotide. As noted above, in some examples, certain capture primers and orthogonal capture primers may include non-nucleotide moieties. Such non-nucleotide moieties may include, but are not limited to, excision moieties via which a portion of the capture primers selectively may be removed, or blocking groups such as described further below with reference to FIGS. 4A-4L. For example, as shown in FIGS. 3A-3I, orthogonal capture primers 332 of the first plurality of orthogonal capture primers may include excision moieties 333, and capture primers 341 of the second plurality of capture primers may include excision moieties 343. Excision moieties 333, 343 may be located at any suitable position along the length of any suitable primer(s) and may be, but need not necessarily be, the same type of excision moiety as one another. Following a desired number of additional amplification operations such as described with reference to FIGS. 3E-3I, portions of orthogonal capture primers 332 of the first plurality of orthogonal capture primers may be removed by reacting a suitable enzyme or reagent with excision moieties 333, and portions of capture primers 341 of the second plurality of capture primers may be removed by reacting a suitable enzyme or reagent with excision moieties 343. The enzyme or reagent used with excision moieties 333 may be the same as, or different than, the enzyme or reagent used with excision moieties 343. As illustrated in FIG. 3J, reaction of excision moieties 333 removes polynucleotides of one orientation in the first substrate region 301, and reaction of excision moieties 334 removes polynucleotides of the other orientation in the second substrate region 302, such that simultaneous paired-end reads may be performed in the two substrate regions. The resulting linearized amplicons in the first and second substrate regions 301, 302 may be at least functionally monoclonal, and may be substantially monoclonal.

Other methods of generating substantially monoclonal regions of a substrate are provided herein. Illustratively, in other examples provided herein, seeding with target polynucleotides and amplification is performed in a first region of the substrate, while the primers in a second region of the substrate may be blocked so that such amplification may not initially be performed in that region. The primers in the second region then are unblocked. The target polynucleotide which has been amplified the most in the first region, may be expected to be further amplified in the second region, thus improving monoclonality.

For example, FIGS. 4A-4L schematically illustrate example compositions and operations in a process flow for amplifying a polynucleotide using unblocked primers in a first substrate region and removably blocked primers in a second substrate region. Composition 4000 illustrated in FIG. 4A includes substrate 400 which includes first region 401 and second region 402 which may be similar to those described with reference to FIG. 3A. First plurality of capture primers 431 may be coupled to first region 401 of substrate 400, and first plurality of orthogonal capture primers 432 may be coupled to the first region 401 of substrate 400. Second plurality of capture primers 441 may be coupled to second region 402 of substrate 400, and second plurality of orthogonal capture primers 442 may be coupled to second region 402 of substrate. In the example illustrated in FIG. 4A, all of the primers may be the same lengths as one another. For example, the capture primers 431 of the first plurality of capture primers may be approximately the same length as the capture primers 441 of the second plurality of capture primers. The capture primers 441 of the second plurality of capture primers may be approximately the same length as the orthogonal capture primers 432 of the first plurality of orthogonal capture primers. Alternatively, the capture primers and orthogonal capture primers may be different lengths than one another in different regions of the substrate, e.g., in a manner such as described with reference to FIGS. 3A-3J.

A first plurality of removable blocking groups 444 may be coupled to the capture primers 441 of the second plurality of capture primers, and a second plurality of removable blocking groups 445 may be coupled to the orthogonal capture primers 442 of the second plurality of capture primers. As described below, the blocking groups 444, 445 may be used so as to inhibit amplification of any target polynucleotides within second region 402 until amplification within first region 401 is substantially complete; such blocking groups then may be removed so as to allow amplification of only certain amplicons that had been generated in first region 401, thus improving monoclonality within second region 402. In one nonlimiting example, blocking groups 444, 445 include 3'-phosphate groups that may be removed using a suitable enzyme, such as a phosphatase or kinase (in reverse activity). In another nonlimiting example, blocking groups 444, 445 include allyl-T groups terminated by a dideoxynucleotide (ddNTP), and may be removed using a suitable reagent, such as palladium. In another nonlimiting example, blocking groups 444, 445 include 3'-O-azide moieties that may be removed using a suitable reagent, such as a reductant. In another nonlimiting example, blocking groups 444, 445 include 3'-O—$NH_2$ moieties that may be removed using a suitable reagent, such as buffered (pH 5.2) sodium nitrate. In another nonlimiting example, blocking groups 444, 445 include 3'-O-allyl moieties that may be removed using a suitable reagent, such as palladium. In another nonlimiting example, blocking groups 444, 445 include 3'-ester moieties that may be removed using a suitable enzyme, such as an esterase.

Similarly as described with reference to FIGS. 3A-3J, composition 4000 further may include a fluid that includes target polynucleotides 451, 452, 453. Each of target polynucleotides 451, 452, 453 may include first adapter 454 that is complementary to the orthogonal capture primers 432, 442 of the first and second pluralities of orthogonal capture primers, and second adapter 455 that is complementary to the capture primers 431, 441 of the first and second pluralities of capture primers. In the nonlimiting example illustrated in FIG. 4A, first adapters 454 of the target polynucleotides 451, 452, 453 are about the same length as the orthogonal capture primers 432, 442 of the first and second pluralities of orthogonal capture primers, and second adapters 455 of the target polynucleotides 451, 452, 453 are about the same length as the capture primers 431, 441 of the first and second pluralities of orthogonal capture primers.

In one purely illustrative example, the capture primers 431, 441 of the first and second pluralities of capture primers are P5 capture primers, and the orthogonal capture primers 432, 443 of the first and second pluralities of orthogonal capture primers are P7 capture primers such as described above. The first adapters 454 may be cP7 adapters, and the second adapters 455 may be cP5 adapters such as described above. The capture primers, orthogonal capture primers, and adapters all may be full length sequences, or certain ones of which may be shortened in a manner such as described with reference to FIGS. 3A-3J.

In a manner similar to that described with reference to FIG. 3B, the adapters 454, 455 of the target polynucleotides may hybridize to random, respective ones of the capture primers 431, 441 or orthogonal capture primers 432, 442, e.g., in accordance with the Poisson distribution. For example, first adapter 454 of target polynucleotide 451 may hybridize to an orthogonal capture primer 432 of the first plurality of orthogonal capture primers to form duplex 461; first adapter 454 of target polynucleotide 453 may hybridize to an orthogonal capture primer 432 of the first plurality of orthogonal capture primers to form duplex 463; and second adapter 455 of target polynucleotide 452 may hybridize to a capture primer 442 of the second plurality of capture primers to form duplex 462. The duplexes resulting from such initial hybridizations between adapters and capture primers or orthogonal capture primers may have melting temperatures (Tm) of greater than about 40° C., e.g., of greater than about 45° C., or of greater than about 50° C., or of greater than about 55° C., or of greater than about 60° C., or of greater than about 65° C., or of greater than about 70° C., e.g., may be relatively stable at the reaction temperature or other temperature at which composition 4000 is held. As described below, target polynucleotides 451, 453 readily may be amplified within first substrate region 401, while blocking groups 444, 445 in second substrate region 402 may inhibit amplification of target polynucleotide 402.

Figure 4A:
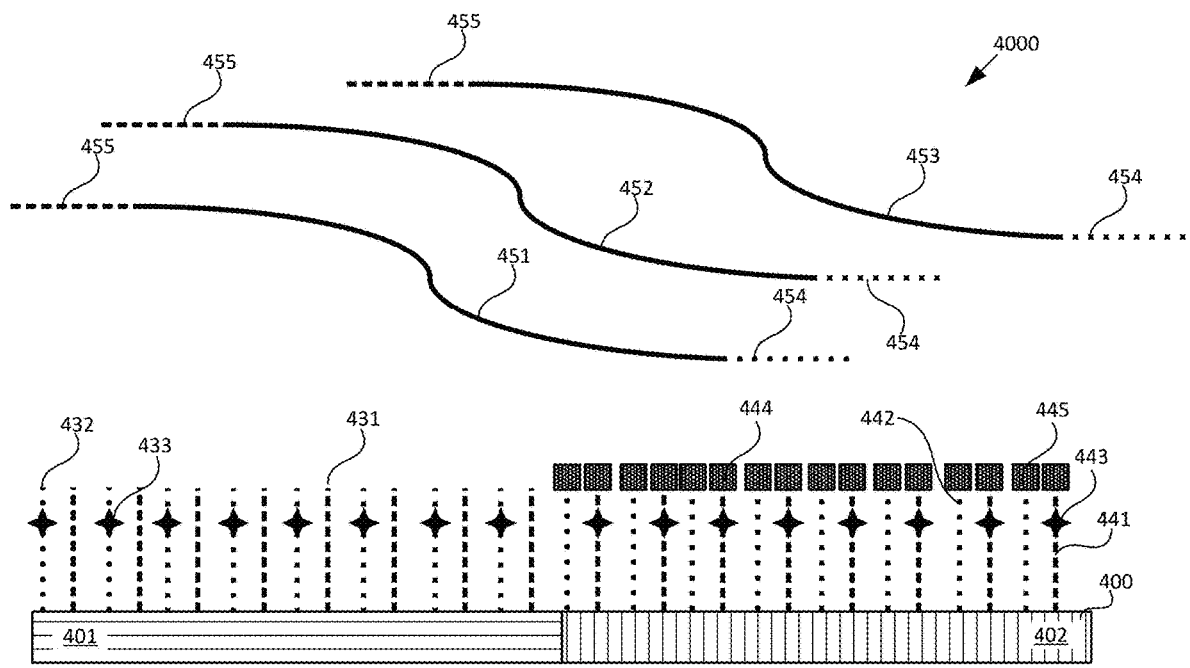
FIGS. 4A-4L schematically illustrate example compositions and operations in a process flow for amplifying a polynucleotide using unblocked primers in a first substrate region and removably blocked primers in a second substrate region.
Figure 4B:
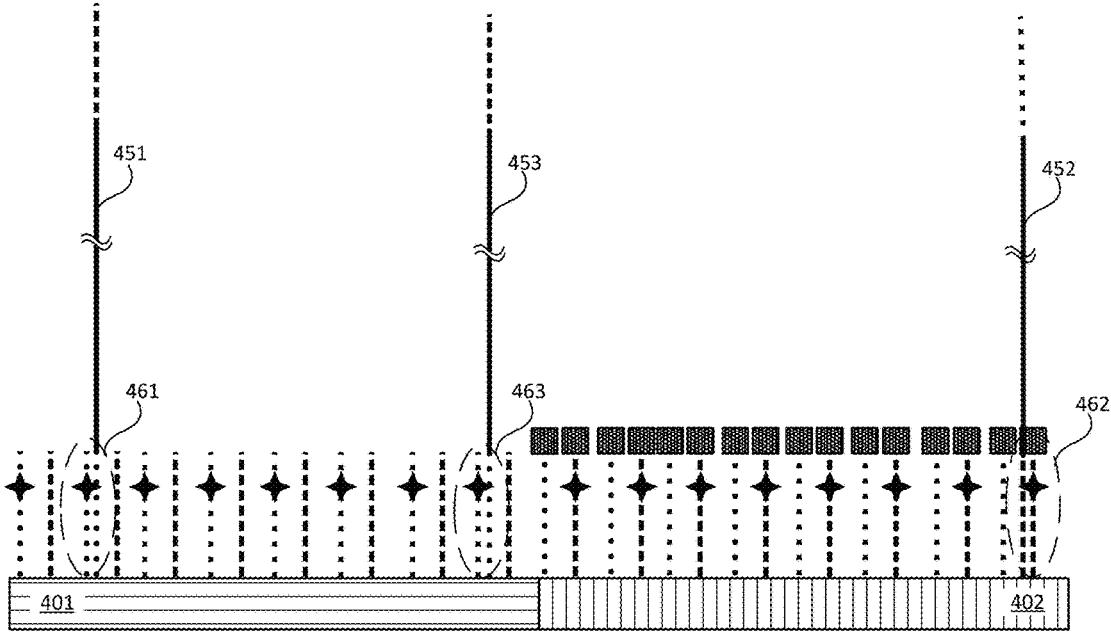
Figure 4C:
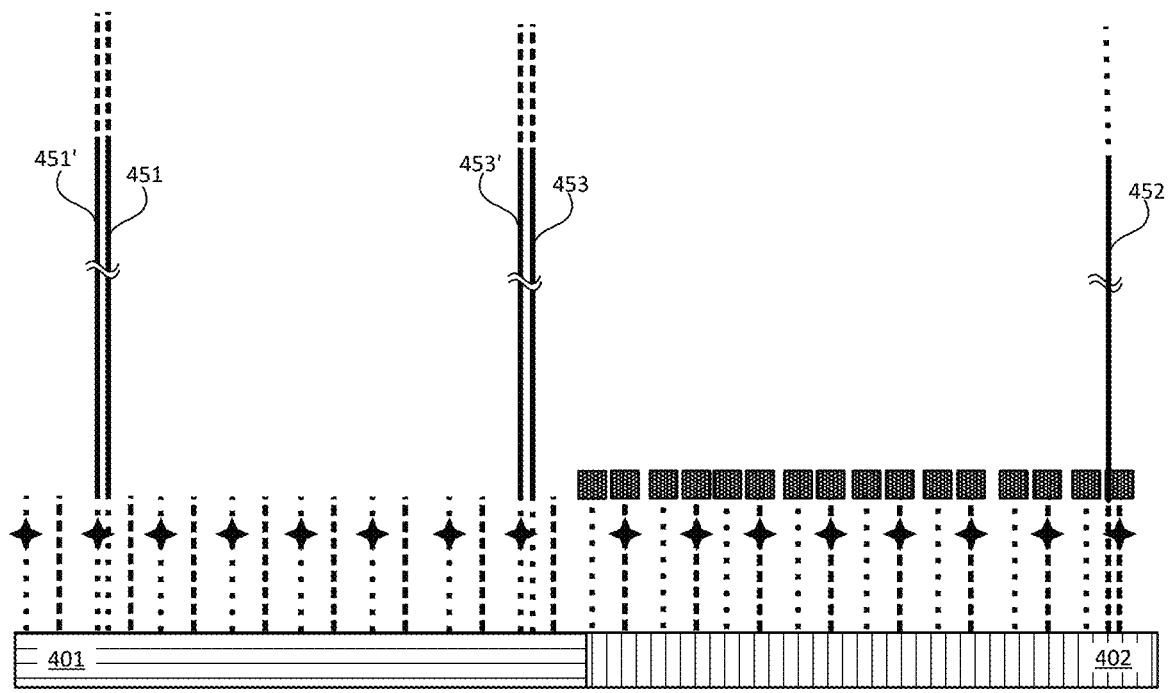
Figure 4D:
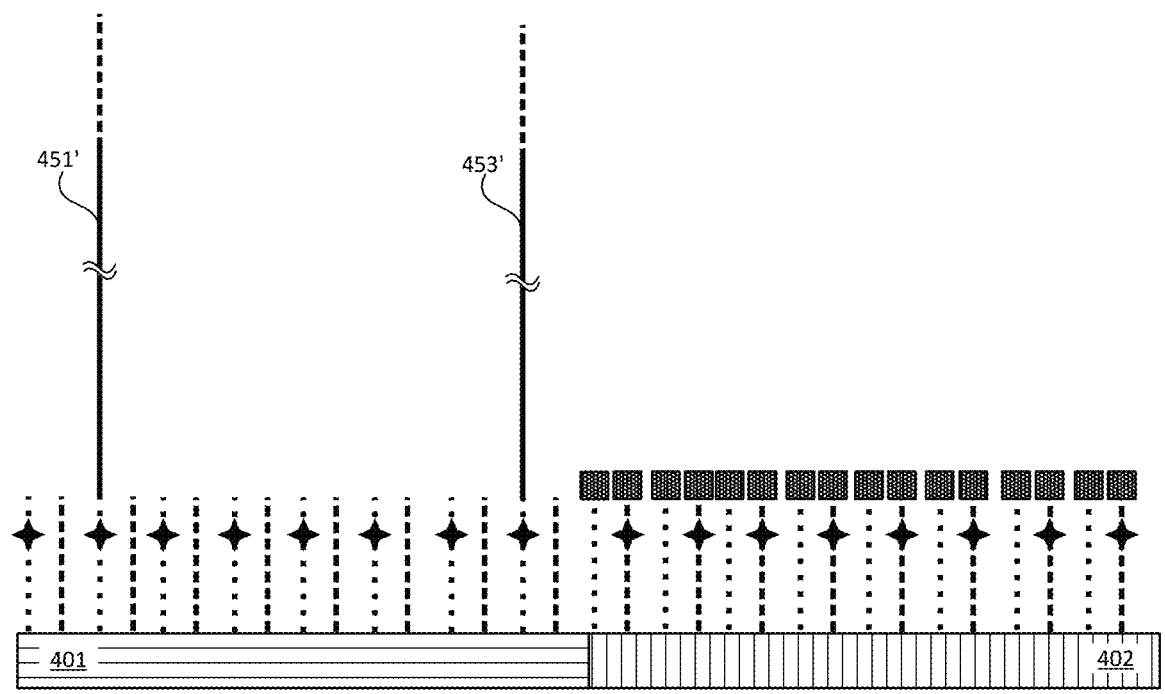

For example, as illustrated in FIG. 4C, after the initial hybridizations described with reference to FIG. 4B, first and third target polynucleotides 451, 453 may be amplified, e.g., forming first amplicon 451' and third amplicon 453' respectively, while blocking group 444 may inhibit amplification of second target polynucleotide 452. Following such amplification, the first, second, and third target polynucleotides 451, 452, 453 may be dehybridized in a manner such as illustrated in FIG. 4D, while first and third amplicons 451', 453' remain covalently bound to substrate 400.

Figure 4E:
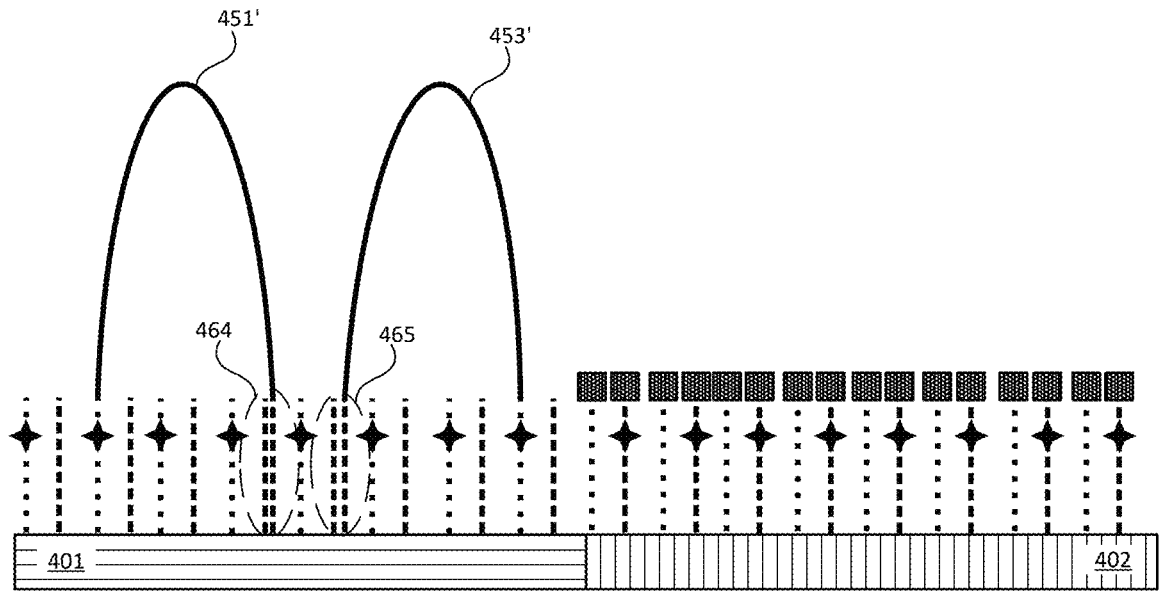

As illustrated in FIG. 4E, second adapter 455 of first amplicon 451' may hybridize to a capture primer 431 of the first plurality of orthogonal capture primers to form duplex 464. Second adapter 455 of third amplicon 453' may hybridize to a capture primer 431 of the first plurality of capture primers to form duplex 465. In a manner similar to that described with reference to FIG. 3E, the hybridization of the second adapters 455 of amplicons 451', 453' to capture primers 431 may promote amplification of amplicons 451', 45'3. For example, the duplexes resulting from the hybridization between respective adapters 455 of amplicons 451', 453' and capture primers 431 may have a melting temperature (Tm) of greater than about 40° C., e.g., of greater than about 45° C., or of greater than about 50° C., or of greater than about 55° C., or of greater than about 60° C., or of greater than about 65° C., or of greater than about 70° C. As such, at the reaction temperature for the amplification, duplexes 464, 465 (as well as duplexes 461, 463 described with reference to FIG. 4B) are likely to be formed for a sufficient amount of time for a polymerase (not specifically illustrated) to begin to form respective amplicons of amplicons 451', 453' using the capture primers or orthogonal capture primers as primers for such amplification.

Figure 4F:
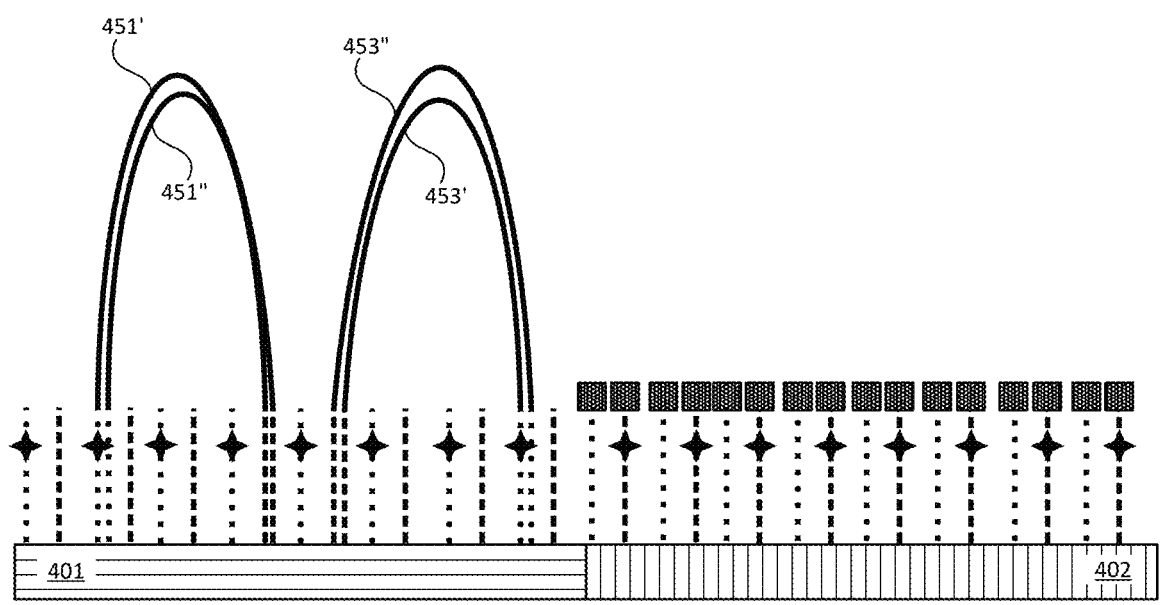

As shown in in FIG. 4F, an amplification operation generates additional amplicon 451" of amplicon 451' and additional amplicon 453" of amplicon 453', while second substrate region 402 may not include any amplicons that may be further amplified. For example, even if the first adapter 455 of one of the target polynucleotides (or amplicons) is hybridized to one of the orthogonal capture primers 442, the removable blocking group 445 coupled to that orthogonal capture primer, may inhibit amplification of that target polynucleotide (or amplicon). As another example, even if the second adapter of one of the target polynucleotides (or amplicons) is hybridized to one of the capture primers 441, the removable blocking group 444 coupled to that capture primer may inhibit amplification of that target polynucleotide (or amplicon). For example, the blocking group 444, 445 may inhibit a polymerase from being able to begin to form an amplicon of the target polynucleotide (e.g., target polynucleotide 452) using the capture primer 441 or orthogonal capture primer 442 as a primer for such amplification. Note that such inhibition of amplification alternatively may be achieved using only one of removable blocking group 444 and removable blocking group 445, or using both of removable blocking group 444 and removable blocking group 445.

Figure 4G:
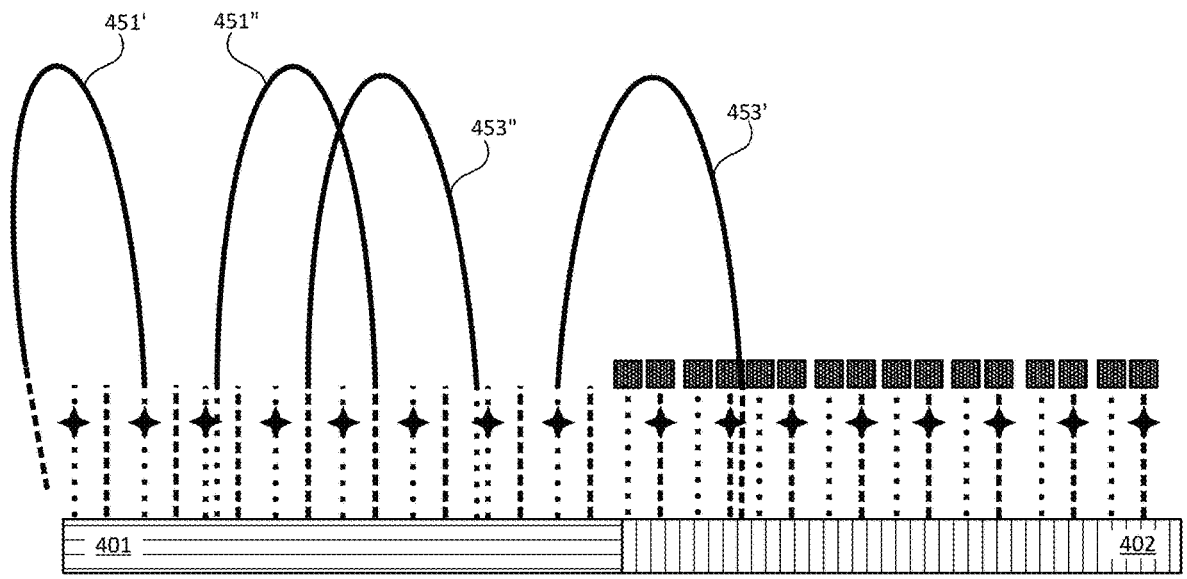
Figure 4H:
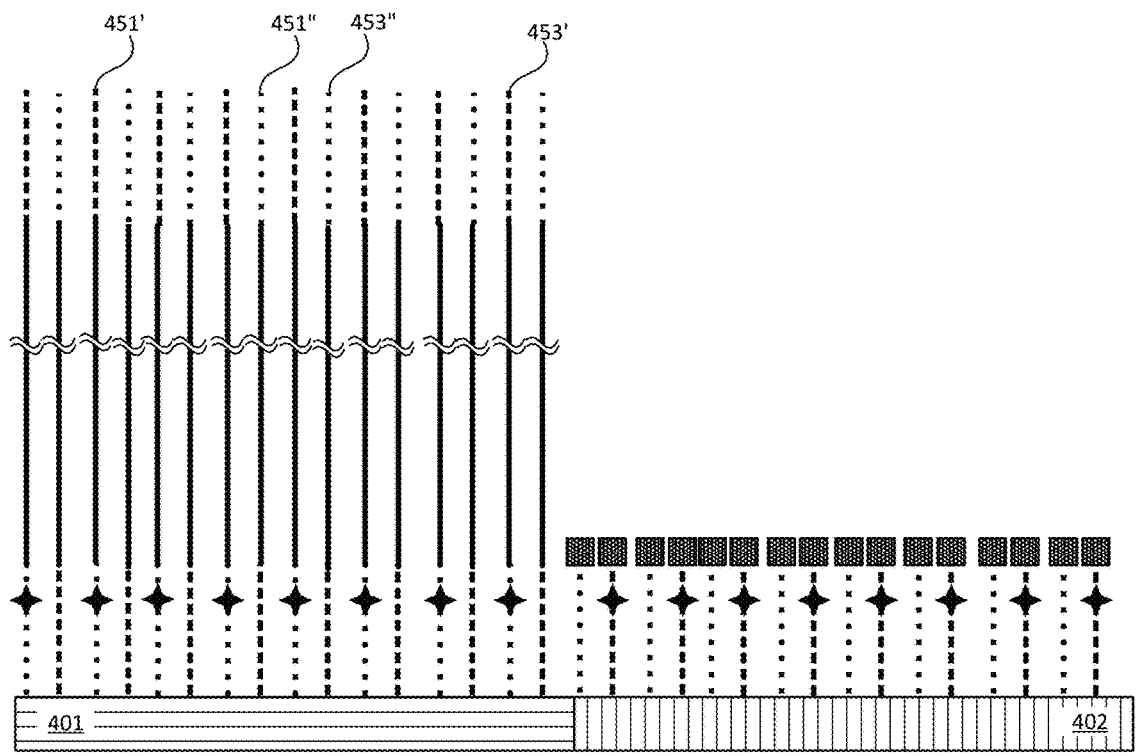

Further amplification operations may be used to generate further amplicons of target polynucleotide(s) in first substrate region 401, while blocking groups 444, 445 continue to inhibit amplification in the second substrate region 402. For example, as shown in FIG. 4G, adapters of amplicons 451', 451", 453', 453" may become hybridized to different capture primers or orthogonal capture primers, and subsequently amplified to produce still further amplicons such as illustrated in FIG. 4H. If amplification operations are repeated until first substrate region 401 is full, both adapters of the target polynucleotides and amplicons may not necessarily be hybridized to corresponding capture primers or orthogonal capture primers, and as such the target polynucleotides and amplicons may extend linearly away from the substrate.

Figure 4I:
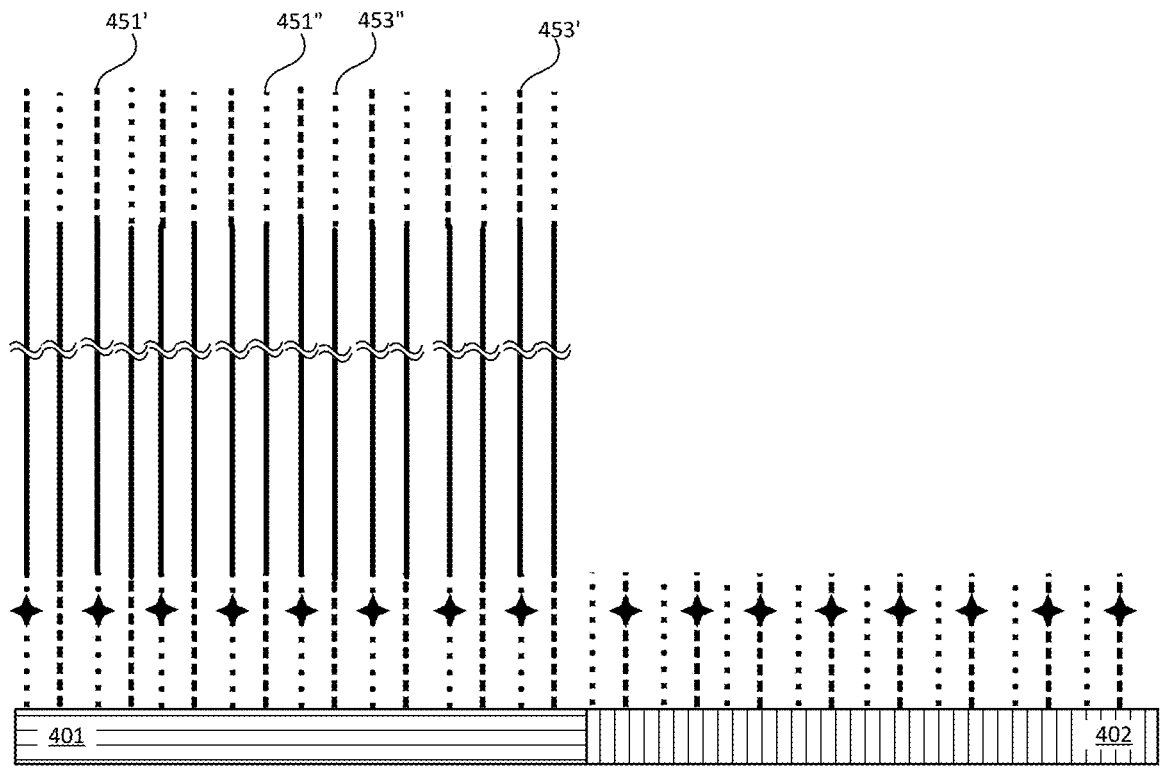
Figure 4J:
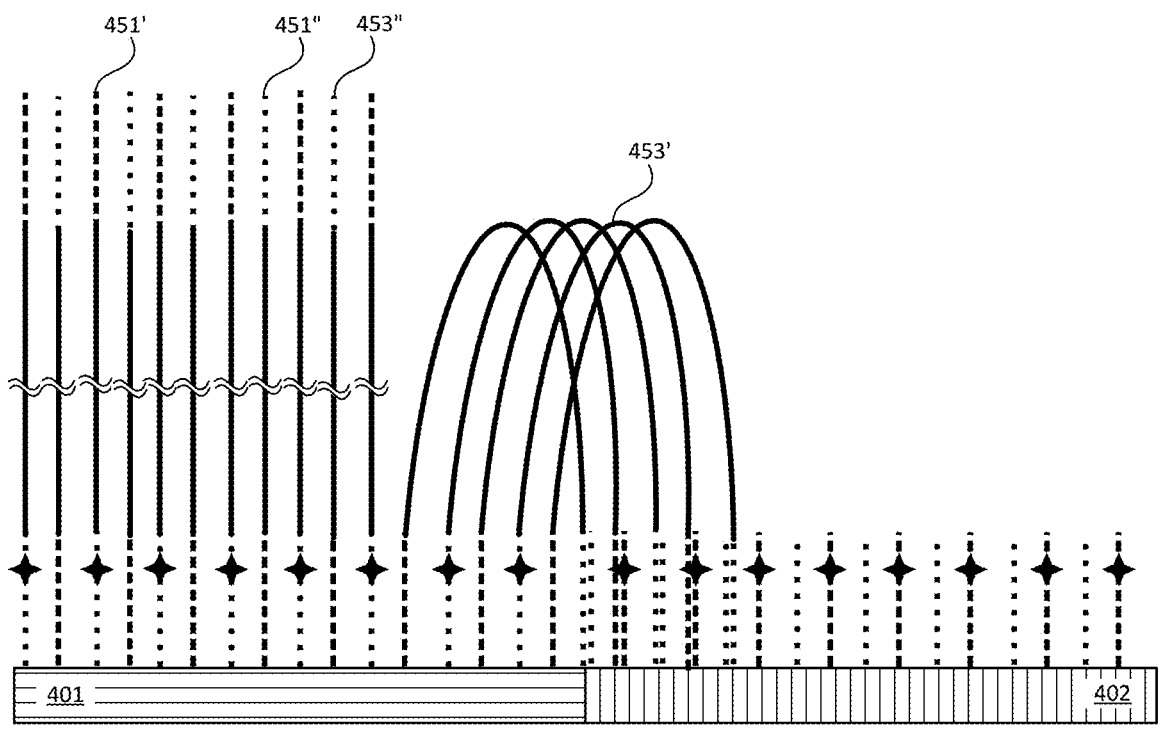
Figure 4K:
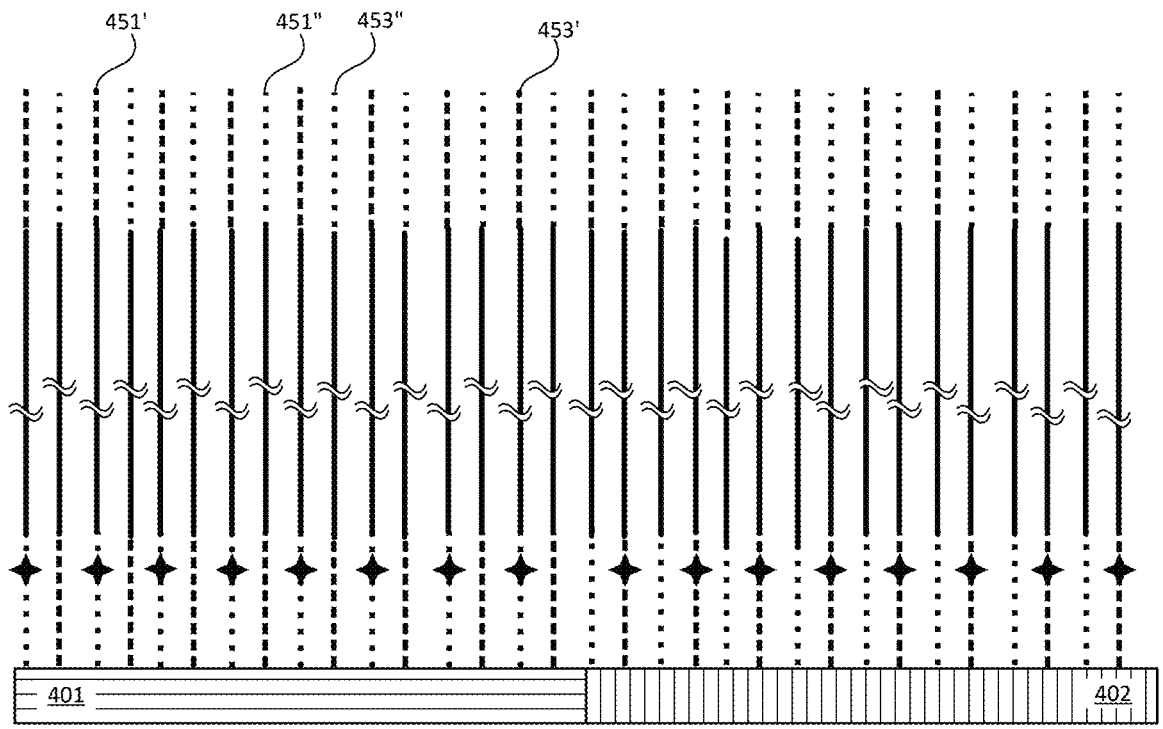

After such amplifying, the first plurality of removable blocking groups 444 may be removed, and the second plurality of removable blocking groups 445 may be removed, such as shown in FIG. 4I. Removal of blocking groups 444 may be concurrent with removal of blocking groups 445, e.g., if blocking groups 444, 445 include the same type of moiety as one another. Alternatively, blocking groups 444 may be removed in a separate step than blocking groups 445, e.g., if blocking groups 444, 445 include different types of moieties than one another. As illustrated in FIG. 4J, subsequent to removing the first and second pluralities of removable blocking groups 444, 445, the first adapter 454 of an amplicon of one of target polynucleotides 451, 453 is hybridized to an orthogonal capture primer 442 of the second plurality of orthogonal capture primers, e.g., an orthogonal capture primer that previously was blocked. Additionally, as illustrated in FIG. 4J, subsequent to removing the first and second pluralities of removable blocking groups 444, 445, the second adapter of an amplicon of one of the target polynucleotides 451, 453 is hybridized to capture primer 441 of the second plurality of capture primers, e.g., a capture primer that previously was blocked. Accordingly, it may be understood that removing the blocking groups from capture primers 441 and orthogonal capture primers 442 makes second substrate region 402 available for further amplifications of amplicons that were generated using first substrate region 401. The various amplicons may be further amplified, resulting a composition such as illustrated in FIG. 4K.

Figure 4L:
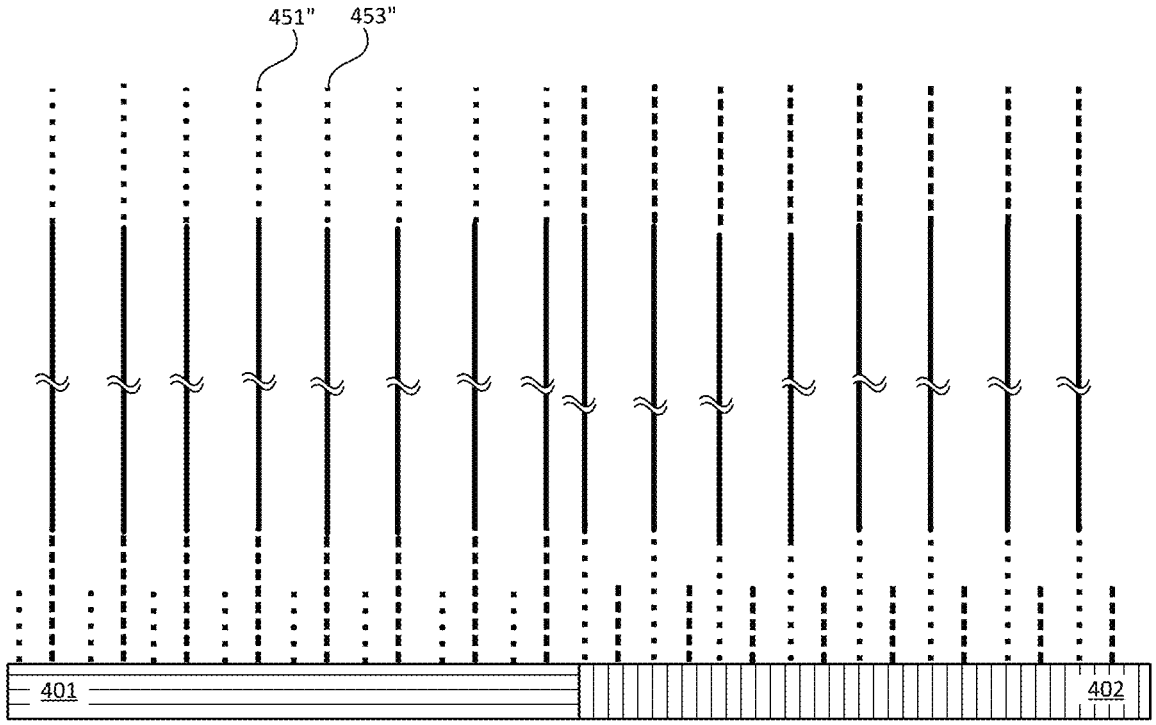

Additionally, in a manner similar to that described with reference to FIGS. 3A-3J, capture primers 431 of the first plurality of capture primers may include excision moieties 433, and the orthogonal capture primers 442 of the second plurality of orthogonal capture primers may include excision moieties 433. Excision moieties 433, 443 may be, but need not necessarily be, the same type of excision moiety as one another. Following a desired number of amplification operations such as described with reference to FIGS. 4F-4K, portions of capture primers 431 of the first plurality of capture primers may be removed by reacting a suitable enzyme or reagent with excision moieties 433, and portions of orthogonal capture primers 442 of the second plurality of orthogonal capture primers may be removed by reacting a suitable enzyme or reagent with excision moieties 443. The enzyme or reagent used with excision moieties 433 may be the same as, or different than, the enzyme or reagent used with excision moieties 443. As illustrated in FIG. 4L, reaction of excision moieties 433 removes polynucleotides of one orientation in the first substrate region 401, and reaction of excision moieties 434 removes polynucleotides of the other orientation in the second substrate region 402, such that simultaneous paired-end reads may be performed in the two substrate regions. Each of substrate regions 401, 402 may be sufficiently monoclonal as to permit simultaneous paired-end reads. For example, amplicons within each of first and second substrate regions 401, 402 each may include at least about 60% amplicons of one selected target polynucleotide, or at least about 70% amplicons of one selected target polynucleotide, or at least about 80% amplicons of one selected target polynucleotide, or at least about 90% amplicons of one selected target polynucleotide, or at least about 95% amplicons of one selected target polynucleotide, or at least about 98% amplicons of one selected target polynucleotide, or at least about 99% amplicons of one selected target polynucleotide, or about 100% amplicons of one selected target polynucleotide.

Although the examples described with reference to FIGS. 3A-3J and FIGS. 4A-4L are illustrated so as to suggest the use of flat substrates with first and second regions that are adjacent to one another, it should be apparent that more complex substrates may be used. For example, FIGS. 5A-5D schematically illustrate additional example compositions for use in amplifying a polynucleotide using primers of different lengths in first and second substrate regions. Compositions such as described with reference to FIGS. 5A-5D may be used in a manner similar to those described with reference to FIGS. 3A-3J, e.g., so as to bias amplification to be more efficient in a selected area. In the example shown in cross-section in FIG. 5A and in plan view in FIG. 5C, substrate 500 may include one or more vertical sidewalls 503 providing a well in which a first region 501 of the substrate surrounds the second region 502 of the substrate (e.g., vertical sidewall 503 may be substantially cylindrical and surround both first region 501 and second region 502, first region 501 may be substantially annular, and second region 502 may be substantially circular). Alternatively, the second region 502 of the substrate may surround the first region 501 of the substrate (e.g., vertical sidewall 503 may be substantially cylindrical and surround both first region 501 and second region 502, second region 502 may be substantially annular, and first region 501 may be substantially circular). As still a further alternative, vertical sidewall 503 may be omitted, and substrate 500 may be substantially planar in the illustrated regions. It will be appreciated that first and second regions 501, 502 may have any suitable shape and position relative to one another. For example, second region 502 need not necessarily be substantially circular and need not necessarily be disposed in the middle of first region 501. Similarly, first region 501 need not necessarily be substantially annular and need not necessarily surround second region symmetrically. In any such example, in a manner similar to that described with reference to FIG. 3A, relatively short capture primers and orthogonal capture primers may be coupled to substrate 500 in first region 501, while longer (e.g., full length) capture primers and orthogonal capture primers may be coupled to substrate 500 in second region 502. As such, amplification may be biased to be more efficient in second region 502, which may be centrally located and where longer primers are attached to substrate 500.

Figure 5A:
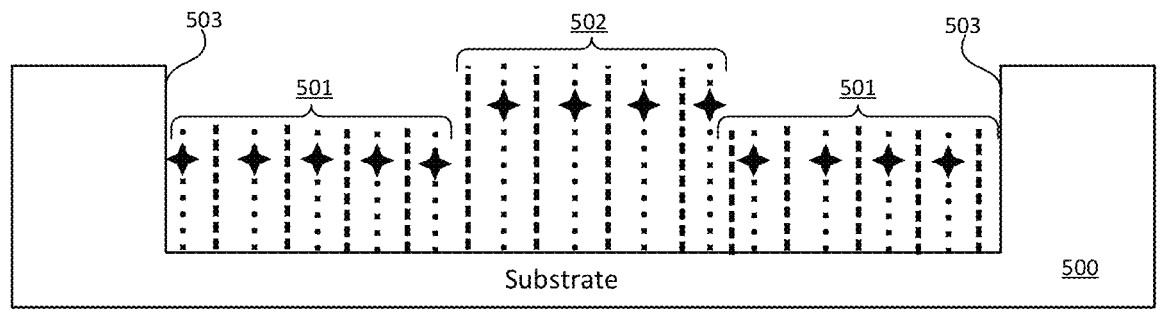
FIGS. 5A-5D schematically illustrate additional example compositions for use in amplifying a polynucleotide using primers of different lengths in first and second substrate regions.
Figure 5B:
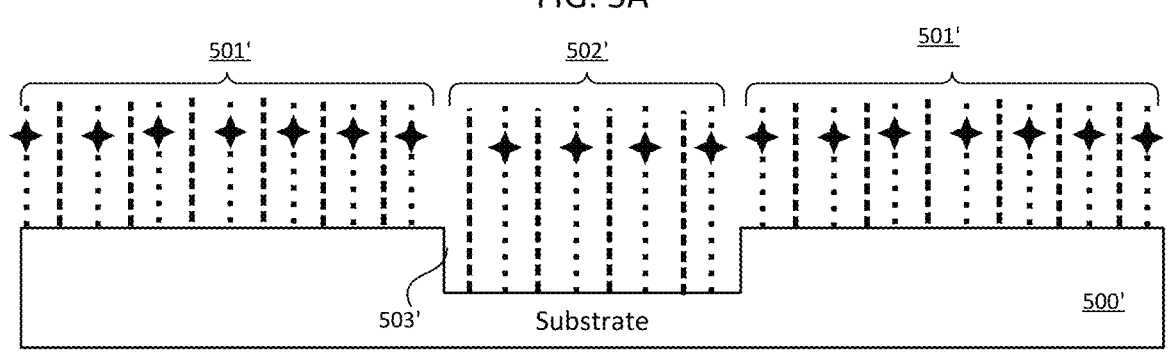
Figure 5C:
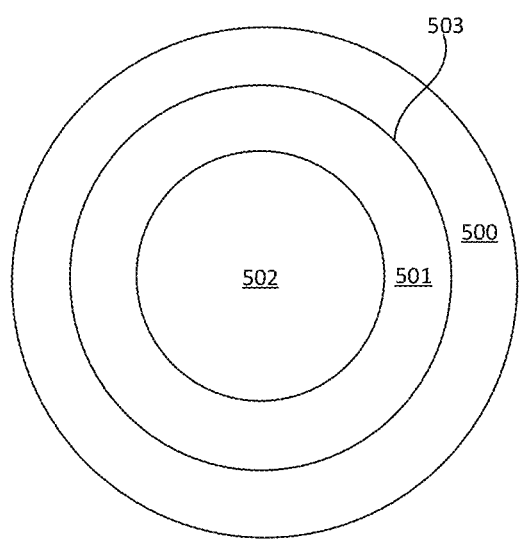
Figure 5D:
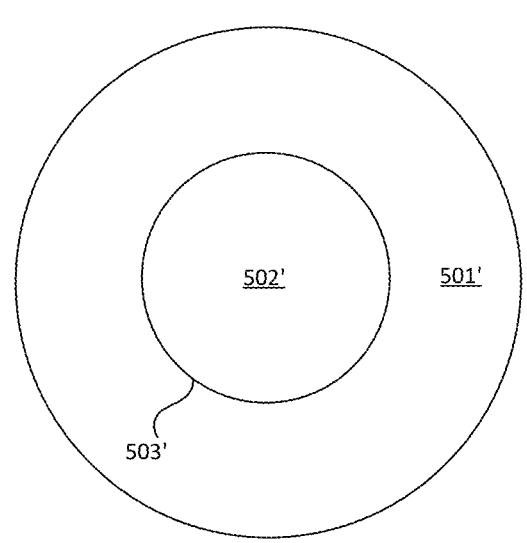

In the example shown in cross-section in FIG. 5B and in plan view in FIG. 5D, substrate 500' may include one or more vertical sidewalls 503' providing a well that encompasses second region 502' of the substrate, and that is surrounded by first region 501' of the substrate (e.g., vertical sidewall 503' may be substantially cylindrical and surround substantially circular second region 502', while first region 501' may be substantially annular and surround vertical sidewall 503' and second region 502'). Alternatively, the first region 501' of the substrate may surround the second region 502' of the substrate (e.g., vertical sidewall 503' may be substantially cylindrical and surround substantially circular first region 501', while second region 502' may be substantially annular and surround vertical sidewall 503' and first region 501'). As still a further alternative, vertical sidewall 503' may be omitted, and substrate 500 may be substantially planar in the illustrated regions. It will be appreciated that first and second regions 501', 502' may have any suitable shape and position relative to one another. For example, second region 502' need not necessarily be substantially circular and need not necessarily be disposed in the middle of first region 501'. Similarly, first region 501' need not necessarily be substantially annular and need not necessarily surround second region symmetrically. In any such example, in a manner similar to that described with reference to FIG. 3A, relatively short capture primers and orthogonal capture primers may be coupled to substrate 500 in first region 501', while longer (e.g., full length) capture primers and orthogonal capture primers may be coupled to substrate 500' in second region 502'. As such, amplification may be biased to be more efficient in second region 502', which may be centrally located and where longer primers are attached to substrate 500'.

FIGS. 6A-6D schematically illustrate additional example compositions for use in amplifying a polynucleotide using unblocked primers in a first substrate region and removably blocked primers in a second substrate region. Compositions such as described with reference to FIGS. 6A-6D may be used in a manner similar to those described with reference to FIGS. 4A-4L, e.g., so as to bias amplification to be more efficient in a selected area. In the example shown in cross-section in FIG. 6A and in plan view in FIG. 6C, substrate 600 may include one or more vertical sidewalls 603 providing a well in which a first region 601 of the substrate surrounds the second region 602 of the substrate (e.g., vertical sidewall 603 may be substantially cylindrical and surround both first region 601 and second region 602, first region 601 may be substantially annular, and second region 602 may be substantially circular). Alternatively, the second region 602 of the substrate may surround the first region 601 of the substrate (e.g., vertical sidewall 603 may be substantially cylindrical and surround both first region 601 and second region 602, second region 602 may be substantially annular, and first region 601 may be substantially circular). As still a further alternative, vertical sidewall 603 may be omitted, and substrate 600 may be substantially planar in the illustrated regions. It will be appreciated that first and second regions 601, 602 may have any suitable shape and position relative to one another. For example, second region 602 need not necessarily be substantially circular and need not necessarily be disposed in the middle of first region 601. Similarly, first region 601 need not necessarily be substantially annular and need not necessarily surround second region symmetrically. In any such example, in a manner similar to that described with reference to FIG. 4A, capture primers and orthogonal capture primers having blocking groups coupled thereto may be coupled to substrate 600 in first region 601, while unblocked capture primers and orthogonal capture primers may be coupled to substrate 600 in second region 602. As such, amplification may be biased to be more efficient in second region 602, which may be centrally located and where blocking groups 601 are omitted.

Figure 6A:
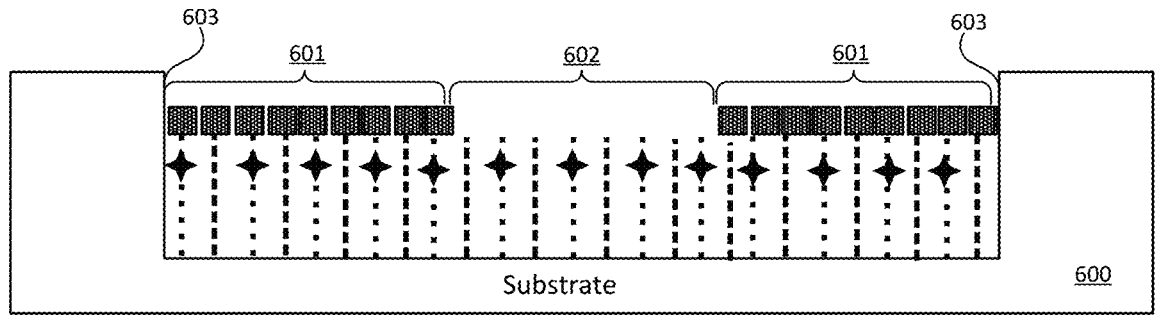
FIGS. 6A-6D schematically illustrate additional example compositions for use in amplifying a polynucleotide using unblocked primers in a first substrate region and removably blocked primers in a second substrate region.
Figure 6B:
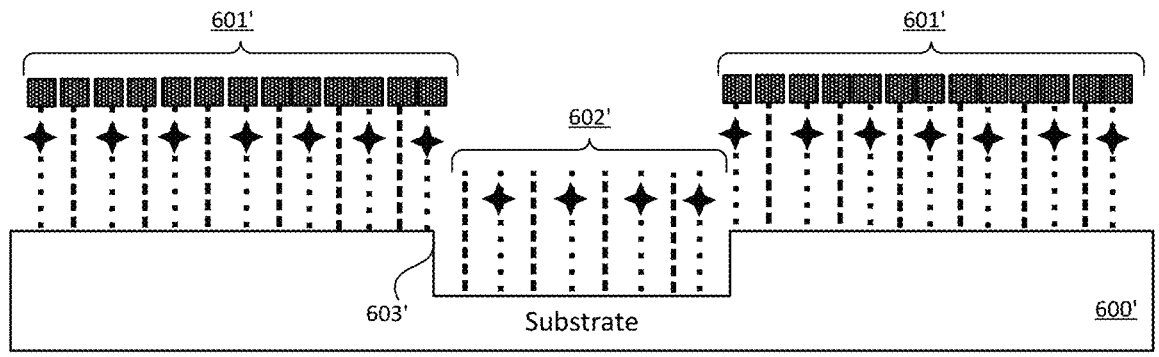
Figure 6C:
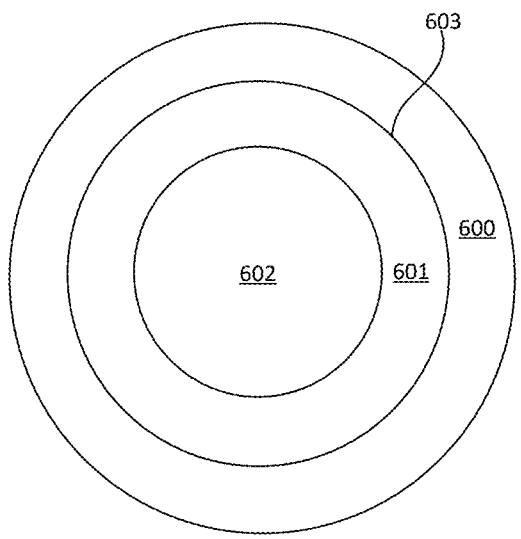
Figure 6D:
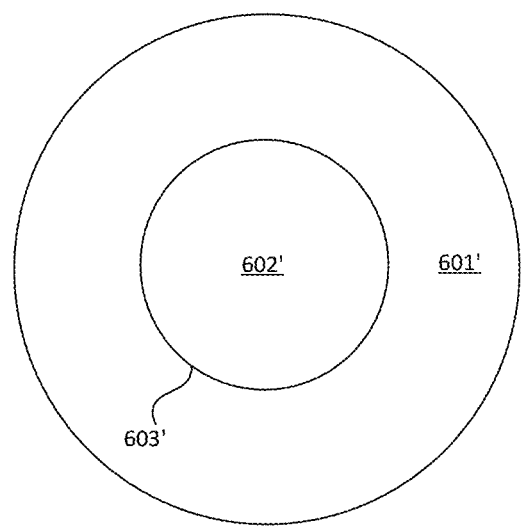

In the example shown in cross-section in FIG. 6B and in plan view in FIG. 6D, substrate 600' may include one or more vertical sidewalls 603' providing a well that encompasses second region 602' of the substrate, and that is surrounded by first region 601' of the substrate (e.g., vertical sidewall 603' may be substantially cylindrical and surround substantially circular second region 602', while first region 601' may be substantially annular and surround vertical sidewall 603' and second region 602'). Alternatively, the first region 601' of the substrate may surround the second region 602' of the substrate (e.g., vertical sidewall 603' may be substantially cylindrical and surround substantially circular first region 601', while second region 602' may be substantially annular and surround vertical sidewall 603' and first region 601'). As still a further alternative, vertical sidewall 603 may be omitted, and substrate 600 may be substantially planar in the illustrated regions. It will be appreciated that first and second regions 601, 602 may have any suitable shape and position relative to one another. For example, second region 602 need not necessarily be substantially circular and need not necessarily be disposed in the middle of first region 601. Similarly, first region 601 need not necessarily be substantially annular and need not necessarily surround second region symmetrically. In any such example, in a manner similar to that described with reference to FIG. 4A, blocked capture primers and blocked orthogonal capture primers may be coupled to substrate 600' in first region 601', while unblocked capture primers and unblocked orthogonal capture primers may be coupled to substrate 600' in second region 602'. As such, amplification may be biased to be more efficient in second region 602', which may be centrally located and where blocking groups 601' are omitted.

Figure 7:
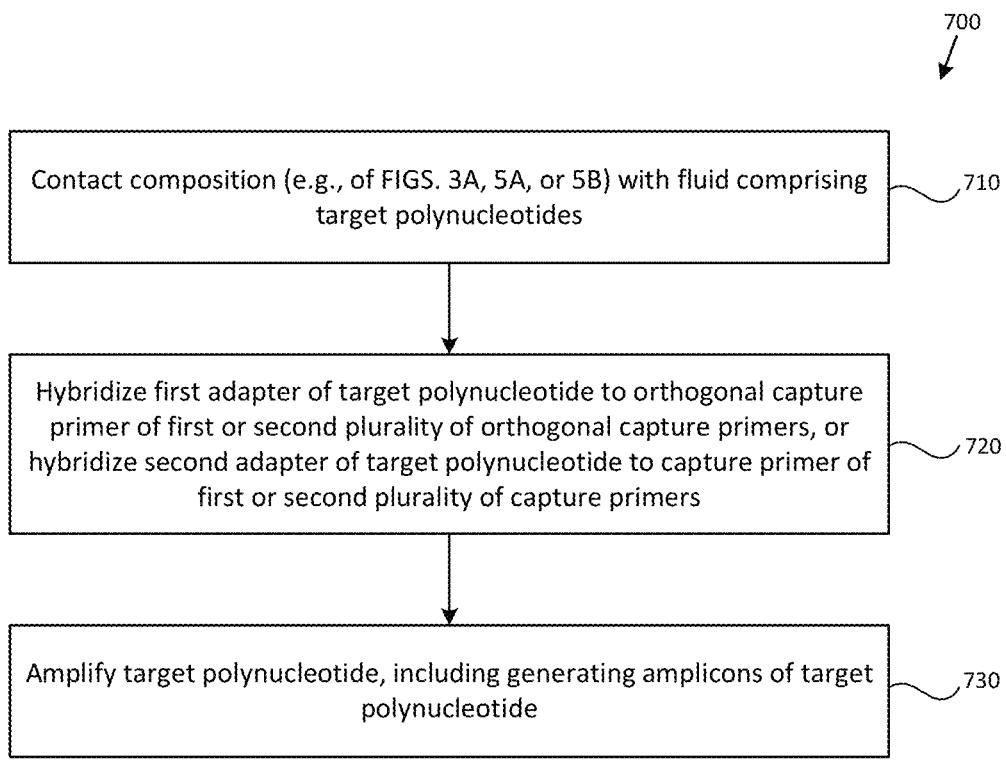
FIG. 7 illustrates an example flow of operations in a method for amplifying a polynucleotide using primers of different lengths in first and second substrate regions.

It will be appreciated that example compositions such as described herein may be used in any suitable method for amplifying a polynucleotide. For example, FIG. 7 illustrates an example flow of operations in a method 700 for amplifying a polynucleotide using primers of different lengths in first and second substrate regions. Although method 700 may be implemented using composition 3000 described with reference to FIGS. 3A-3J or the compositions described with reference to FIGS. 5A-5D, method 700 may be implemented using any other suitable composition.

Referring now to FIG. 7, method 700 includes contacting a composition with a fluid (operation 710). In some examples, the composition may be such as described with reference to FIG. 3A, 5A, or 5B. Illustratively, the composition may include a substrate that includes a first region and a second region, e.g., first region 301, 501, or 501', and second region 302, 502, or 502'. A first plurality of capture primers may be coupled to the first region of the substrate, e.g., capture primers 331, or the capture primers within first region 501 or 501'. A second plurality of capture primers may be coupled to the second region of the substrate, e.g., capture primers 341, or the capture primers within second region 502 or 502'. The capture primers of the second plurality of capture primers may be longer than the capture primers of the first plurality of capture primers. A first plurality of orthogonal capture primers may be coupled to the first region of the substrate, e.g., orthogonal capture primers 332, or the orthogonal capture primers within first region 501 or 501'. A second plurality of orthogonal capture primers may be coupled to the second region of the substrate, e.g., orthogonal capture primers 342, or the orthogonal capture primers within second region 502 or 502'. The orthogonal capture primers of the second plurality of orthogonal capture primers may be shorter than the orthogonal capture primers of the first plurality of orthogonal capture primers.

The fluid may include target polynucleotides. Each of the target polynucleotides may include a first adapter that is complementary to the orthogonal capture primers of the first and second pluralities of orthogonal capture primers, and a second adapter that is complementary to the capture primers of the first and second pluralities of capture primers, e.g., first and second adapters 354, 355 described with reference to FIG. 3A.

Method 700 further may include hybridizing the first adapter of a first one of the target polynucleotides to an orthogonal capture primer of the first or second plurality of orthogonal capture primers, or hybridizing the second adapter of that target polynucleotide to a capture primer of the first or second plurality of capture primers (operation 720). For example, as described above with reference to FIG. 3B, target polynucleotides may be distributed across the substrate surface, e.g., in accordance with the Poisson distribution. However, as described above with reference to FIGS. 3E-3I, for target polynucleotides that hybridize sufficiently far away from the border between the first and second substrate regions, the shortened capture primers or shortened orthogonal capture primers in that region of the substrate may fully or partially inhibit hybridization of the other adapter of such polynucleotides. In comparison, for a target polynucleotide that hybridizes sufficiently close to the border between the first and second substrate regions multiple amplicons may be generated.

Method 700 further may include amplifying the target polynucleotide, the amplifying including generating amplicons of that target polynucleotide (operation 730). For example, as described above with reference to FIGS. 3E-3I, an amplicon of the target polynucleotide that is sufficiently close to the border between the first and second regions of the substrate readily may be further amplified, while amplicons of target polynucleotides that are sufficiently far from the border may not be further amplified. Illustratively, method 700 may include covalently coupling a first amplicon to one of the orthogonal capture primers of the first plurality of orthogonal capture primers, and completely hybridizing a second adapter of the first amplicon to one of the capture primers of the second plurality of capture primers, e.g., such that the amplicon bridges the border between the first and second regions of the substrate and thus may be further amplified. Alternatively, method 700 may include covalently coupling a second amplicon to one of the capture primers of the first plurality of capture primers, and completely hybridizing a first adapter of the second amplicon to one of the orthogonal capture primers of the second plurality of orthogonal capture primers, e.g., such that the amplicon bridges the border between the first and second regions of the substrate and thus may be further amplified.

Method 700 also may include covalently coupling a third amplicon to one of the orthogonal capture primers of the first plurality of orthogonal capture primers, and being unable to completely hybridize a second adapter of the third amplicon to any of the capture primers of the first plurality of capture primers. The inability of the second adapter to completely hybridize to any of the capture primers of the first plurality of capture primers may amplification of the third amplicon, e.g., that amplicon may not bridge the border between the first and second regions of the substrate. In some examples, any partial duplex between the second adapter of the third amplicon and any of the capture primers of the first plurality of capture primers has a melting temperature (Tm) of less than about 20° C. Method 700 also or alternatively may include covalently coupling a fourth amplicon to one of the capture primers of the second plurality of capture primers, and being unable to completely hybridize a first adapter of the fourth amplicon to any of the orthogonal capture primers of the second plurality of orthogonal capture primers. The inability of the first adapter to completely hybridize to any of the orthogonal capture primers of the second plurality of orthogonal capture primers may amplification of the fourth amplicon. As such, the first or second amplicons may be further amplified, while the third and fourth amplicons may not be further amplified.

Figure 8:
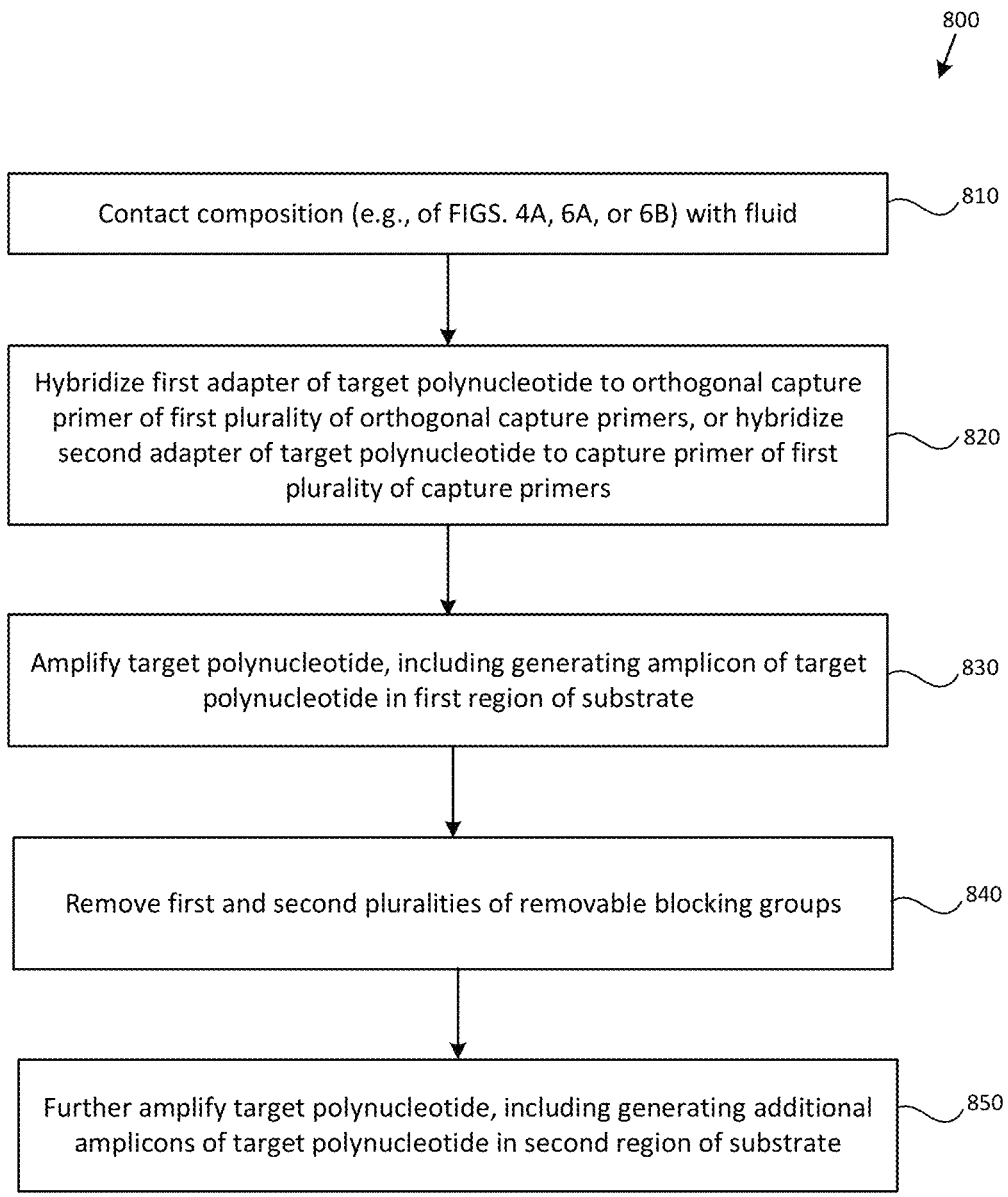
FIG. 8 illustrates an example flow of operations in a method for amplifying a polynucleotide using unblocked primers in a first substrate region and removably blocked primers in a second substrate region.

FIG. 8 illustrates an example flow of operations in a method 800 for amplifying a polynucleotide using unblocked primers in a first substrate region and removably blocked primers in a second substrate region. Although method 800 may be implemented using composition 4000 described with reference to FIGS. 4A-4L or the compositions described with reference to FIGS. 6A-6D, method 800 may be implemented using any other suitable composition.

Referring now to FIG. 8, method 800 may include contacting a composition with a fluid (operation 810). In some examples, in a manner such as described elsewhere herein, the composition may include a substrate that includes a first region and a second region, e.g., first region 401, 601, or 601', and second region 402, 602, or 602'. A first plurality of capture primers may be coupled to the first region of the substrate, e.g., capture primers 431, or the capture primers within first region 601 or 601'. A first plurality of orthogonal capture primers may be coupled to the first region of the substrate, e.g., orthogonal capture primers 432, or the orthogonal capture primers within first region 601 or 601'. A second plurality of capture primers may be coupled to the second region of the substrate, e.g., capture primers 441, or the capture primers within second region 602 or 602'. A second plurality of orthogonal capture primers may be coupled to the second region of the substrate, e.g., orthogonal capture primers 442, or the orthogonal capture primers within second region 602 or 602'. A first plurality of removable blocking groups (e.g., blocking groups 444) may be coupled to the capture primers of the second plurality of capture primers. A second plurality of removable blocking groups (e.g., blocking groups 445) may be coupled to the orthogonal capture primers of the second plurality of capture primers. The fluid may include target polynucleotides. Each of the target polynucleotides may include a first adapter that is complementary to the orthogonal capture primers of the first and second pluralities of orthogonal capture primers, and a second adapter that is complementary to the capture primers of the first and second pluralities of capture primers, e.g., first and second adapters 454, 455 described with reference to FIG. 4A.

Method 800 further may include respectively hybridizing the first adapter of a first one of the target polynucleotides to one of the orthogonal capture primers of the first plurality of orthogonal capture primers, or hybridizing the second adapter of the first one of the target polynucleotides to one of the capture primers of the first plurality of capture primers (operation 820). For example, as described above with reference to FIG. 4B, target polynucleotides may be distributed across the substrate surface, e.g., in accordance with the Poisson distribution, and may hybridize with primers coupled to such regions. One or more of such target polynucleotides may be in regions in which the primers include blocking groups, and one or more of such target polynucleotides (e.g., the first one of the target polynucleotides) may be in regions in which the primers do not include blocking groups.

Method 800 further may include amplifying the first one of the target polynucleotides, the amplifying comprising generating an amplicon of the first one of the target polynucleotides in the first region of the substrate (operation 830). For example, because the primers in the first region of the substrate lack blocking groups, amplification readily may be performed in first region in a manner such as described with reference to FIGS. 4F-4H. For example, method 800 may include covalently coupling an amplicon to one of the orthogonal capture primers of the first plurality of orthogonal capture primers, the amplicon having a second adapter completely hybridized to one of the capture primers of the first plurality of capture primers. That amplicon readily may be further amplified in the first region of the substrate. Alternatively, method 800 may include covalently coupling an amplicon to one of the capture primers of the first plurality of capture primers, the amplicon having a first adapter completely hybridized to one of the orthogonal capture primers of the first plurality of orthogonal capture primers. That amplicon readily may be further amplified in the first region of the substrate.

In comparison, because the primers in the second region of the substrate include blocking groups, amplification may be inhibited in the second region. The blocking groups may inhibit amplification of any target polynucleotides that hybridize in the second region of the substrate. For example, the first adapter of a second one of the target polynucleotides may be hybridized to one of the orthogonal capture primers of the second plurality of orthogonal capture primers, or wherein the second adapter of the second one of the target polynucleotides is hybridized to one of the capture primers of the second plurality of capture primers. The removable blocking group coupled to the one of the capture primers may inhibit amplification of the second one of the target polynucleotides, or the removable blocking group coupled to the one of the orthogonal capture primers may inhibit amplification of the second one of the target polynucleotides.

Method 800 may include removing the first and second pluralities of removable blocking groups (operation 840), e.g., in a manner such as described with reference to FIG. 4I. Method 800 may include then further amplifying the first one of the target polynucleotides, the amplifying comprising generating additional amplicons of the first one of the target polynucleotides in the second region of the substrate (operation 850), e.g., in a manner such as described with reference to FIGS. 4J-4K. It will be appreciated that the present compositions and methods are not limited to use with the particular operations described above. For example, although FIGS. 3A-3J and FIGS. 4A-4L may be considered operations consistent with "bridge amplification" or "surface-bound polymerase chain reaction," it will be appreciated that the present compositions and methods readily may be adapted for use with other amplification modalities. One such amplification modality is "exclusion amplification," or ExAmp. Exclusion amplification methods may allow for the amplification of a single target polynucleotide per substrate region and the production of a substantially monoclonal population of amplicons in a substrate region. For example, the rate of amplification of the first captured target polynucleotide within a substrate region may be more rapid relative to much slower rates of transport and capture of target polynucleotides at the substrate region. As such, the first target polynucleotide captured in a substrate region may be amplified rapidly and fill the entire substrate region, thus inhibiting the capture of additional target polynucleotide in the same substrate region. Alternatively, if a second target polynucleotide attaches to same substrate region after the first polynucleotide, the relatively rapid amplification of the first polynucleotide may fill enough of the substrate region to result in a signal that is sufficiently strong to perform sequencing by synthesis (e.g., the substrate region may be at least functionally monoclonal). The use of exclusion amplification may also result in super-Poisson distributions of monoclonal substrate regions; that is, the fraction of substrate regions in an array that are functionally monoclonal may exceed the fraction predicted by the Poisson distribution.

Increasing super-Poisson distributions of useful clusters is useful because more functionally monoclonal substrate regions may result in higher quality signal, and thus improved SBS; however, the seeding of target polynucleotides into substrate regions may follow a spatial Poisson distribution, where the trade-off for increasing the number of occupied substrate regions is increasing the number of polyclonal substrate regions. One method of obtaining higher super-Poisson distributions is to have seeding occur quickly, followed by a delay among the seeded target polynucleotide. The delay, termed "kinetic delay" because it is thought to arise through the biochemical reaction kinetics, gives one seeded target polynucleotide an earlier start over the other seeded targets. Exclusion amplification works by using recombinase to facilitate the invasion of primers (e.g., primers attached to a substrate region) into double-stranded DNA (e.g., a target polynucleotide) when the recombinase mediates a sequence match. The present compositions and methods may be adapted for use with recombinase to facilitate the invasion of the present capture primers and orthogonal capture primers into the present target polynucleotides when the recombinase mediates a sequence match. Indeed, the present compositions and methods may be adapted for use with any surface-based polynucleotide amplification methods such as thermal PCR, chemically denatured PCR, and enzymatically mediated methods (which may also be referred to as recombinase polymerase amplification (RPA) or ExAmp).

Working Examples

The following examples are intended to be purely illustrative, and not limiting in any way.

Figure 9:
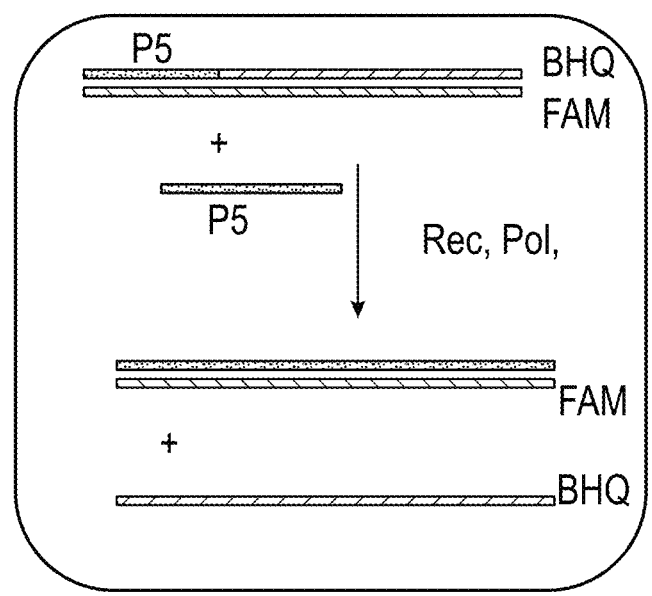
FIG. 9 schematically illustrates a solution-based model composition for characterizing the effect of capture primer length on amplification efficiency.

FIG. 9 schematically illustrates a solution-based model composition for characterizing the effect of capture primer length on amplification efficiency. More specifically, the model composition included a duplex including a first oligonucleotide coupled to the fluorophore (fluorescene, FAM), hybridized to a second oligonucleotide including a P5 primer coupled to a quencher (black hole quencher, BHQ) such that the quencher inhibited fluorescence of the fluorophore. A P5 adapter, a recombinase, a polymerase, and a plurality of nucleotides were used to invade the duplex between the first and second oligonucleotides in a recombinase polymerase amplification (RPA or ExAmp) process, causing extension of the invading P5 primer and dissociation of the second oligonucleotide from the first oligonucleotide, allowing the fluorophore to fluoresce.

Figure 10:
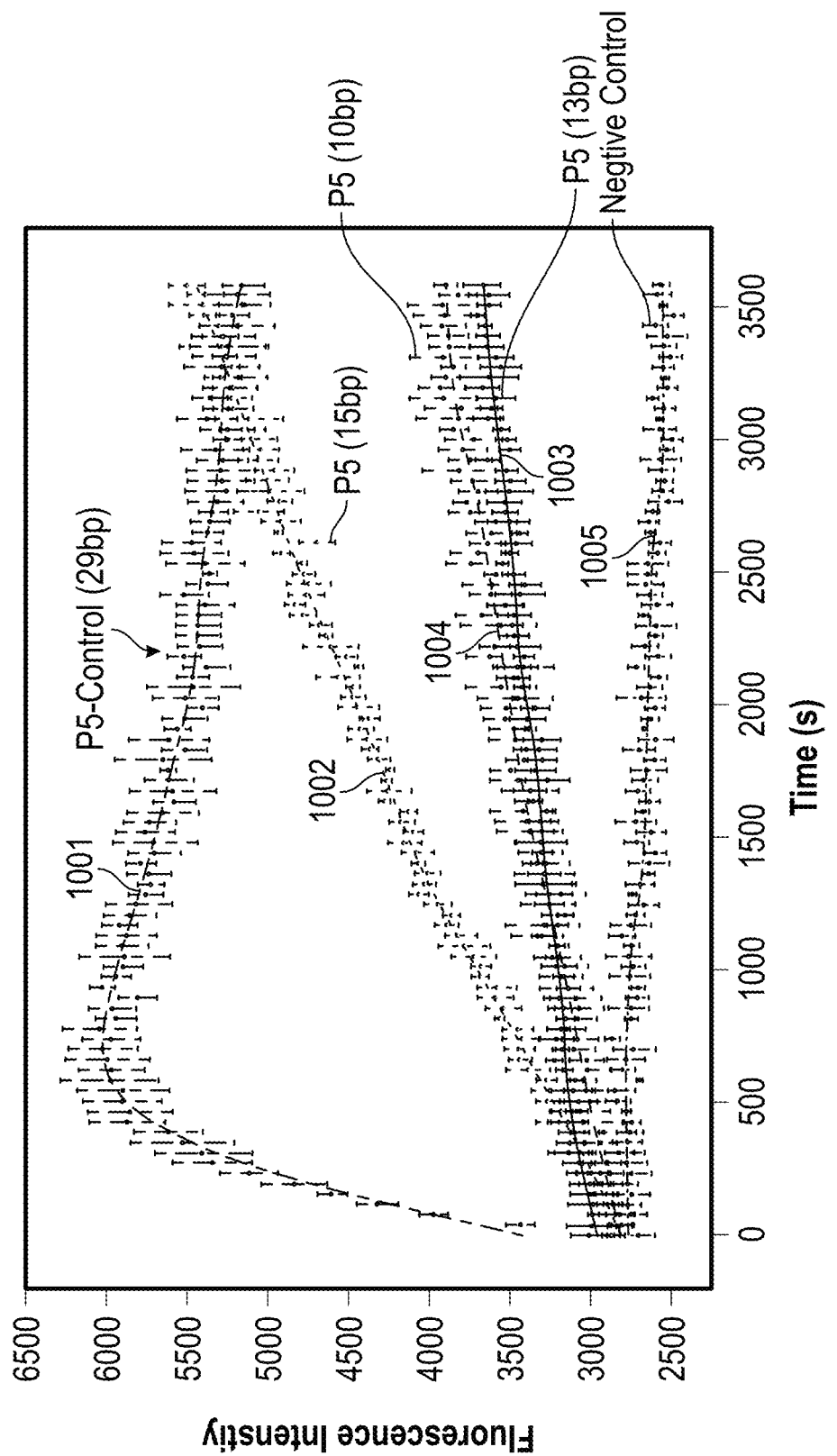
FIG. 10 is a plot illustrating fluorescence intensity resulting from amplification with different capture primer lengths.

FIG. 10 is a plot illustrating fluorescence intensity resulting from amplification with different capture primer lengths. More specifically, trace 1001 is the measured fluorescence intensity from the model composition described with reference to FIG. 9, using a full length P5 primer that was 29 bases long; trace 1002 is the measured intensity from that system using a modified P5 primer that was 15 bases long; trace 1003 is the measured intensity from that system using a modified P5 primer that was 10 bases long; trace 1004 is the measured intensity from that system using a modified P5 primer that was 13 bases long; and trace 1005 is the measured intensity from that system without use of an invading P5 primer (negative control). From FIG. 10, it may be seen that initial fluorescence intensity from the model composition using the full length P5 primer was the highest, indicating that this primer was amplified most effectively which caused the most dissociation of the quencher from the fluorophore. The fluorescence intensity from the model composition using the modified P5 primer that was 15 bases long began at a significantly lower value than that of using the full length P5 primer, but gradually increased to a value similar to that of using the full length P5 primer. The fluorescence intensities from the model compositions using the modified P5 primers that were 13 and 10 bases long, respectively, were similar to one another. The fluorescence intensity from the model composition without use of an invading P5 primer (negative control) was the lowest. From FIG. 10, it may be understood that shorter primers may be expected to have lower amplification efficiency. As such, for compositions such as described with reference to FIGS. 3A-3J, it may be expected that amplification may be expected to be less efficient in regions where target polynucleotides substantially only may access shortened primers, than in the border region where target polynucleotides may access longer primers.

Additional Comments

While various illustrative examples are described above, it will be apparent to one skilled in the art that various changes and modifications may be made therein without departing from the invention. For example, a composition may include any suitable combination of components from composition 3000 and composition 4000, and a method may include any suitable combination of operations from method 700 and method 800. The appended claims are intended to cover all such changes and modifications that fall within the true spirit and scope of the invention.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

What is claimed is:

1. A composition for amplifying a polynucleotide, the composition comprising:
   a substrate comprising a first region and a second region;
   a first plurality of capture primers coupled to the first region of the substrate;
   a second plurality of capture primers coupled to the second region of the substrate, the capture primers of the second plurality of capture primers being longer than the capture primers of the first plurality of capture primers;
   a first plurality of orthogonal capture primers coupled to the first region of the substrate; and
   a second plurality of orthogonal capture primers coupled to the second region of the substrate, the orthogonal capture primers of the second plurality of orthogonal capture primers being shorter than the orthogonal capture primers of the first plurality of orthogonal capture primers.

2. The composition of claim 1, further comprising a fluid comprising target polynucleotides, each of the target polynucleotides comprising a first adapter that is complementary to the orthogonal capture primers of the first and second pluralities of orthogonal capture primers, and a second adapter that is complementary to the capture primers of the first and second pluralities of capture primers.

3. The composition of claim 2, wherein the first adapters of the target polynucleotides are shorter than the orthogonal capture primers of the first plurality of orthogonal capture primers, and wherein the second adapters of the target polynucleotides are shorter than the capture primers of the second plurality of capture primers.

4. The composition of claim 2, wherein the first adapter of a first one of the target polynucleotides is hybridized to a first one of the orthogonal capture primers of the first plurality of orthogonal capture primers, or wherein the second adapter of the first one of the target polynucleotides is hybridized to a first one of the capture primers of the second plurality of capture primers.

5. The composition of claim 4, wherein a duplex formed from the hybridization between the first adapter of the first one of the target polynucleotides and the first one of the orthogonal capture primers has a melting temperature (Tm) of greater than about 40° C.

6. The composition of claim 1, further comprising a first amplicon covalently coupled to one of the orthogonal capture primers of the first plurality of orthogonal capture primers, the first amplicon having a second adapter completely hybridized to one of the capture primers of the second plurality of capture primers.

7. The composition of claim 1, further comprising a second amplicon covalently coupled to one of the capture primers of the first plurality of capture primers, the second amplicon having a first adapter completely hybridized to one of the orthogonal capture primers of the second plurality of orthogonal capture primers.

8. The composition of claim 1, further comprising a third amplicon covalently coupled to one of the orthogonal capture primers of the first plurality of orthogonal capture primers, the third amplicon having a second adapter that is unable to completely hybridize to any of the capture primers of the first plurality of capture primers.

9. The composition of claim 8, wherein the inability of the second adapter to completely hybridize to any of the capture primers of the first plurality of capture primers inhibits amplification of the third amplicon.

10. The composition of claim 9, wherein any partial duplex between the second adapter of the third amplicon and any of the capture primers of the first plurality of capture primers has a melting temperature (Tm) of less than about 20° C.

11. The composition of claim 1, further comprising a fourth amplicon covalently coupled to one of the capture primers of the second plurality of capture primers, the fourth amplicon having a first adapter that is unable to completely hybridize to any of the orthogonal capture primers of the second plurality of orthogonal capture primers.

12. The composition of claim 11, wherein the inability of the first adapter to completely hybridize to any of the orthogonal capture primers of the second plurality of orthogonal capture primers inhibits amplification of the fourth amplicon.

13. The composition of claim 1, wherein the capture primers of the first plurality of capture primers are at least 5 bases shorter than the capture primers of the second plurality of capture primers, and wherein the orthogonal capture primers of the second plurality of orthogonal capture primers are at least 5 bases shorter than the orthogonal capture primers of the first plurality of orthogonal capture primers.

14. The composition of claim 13, wherein the capture primers of the second plurality of capture primers are P5 capture primers, and wherein the orthogonal capture primers of the first plurality of orthogonal capture primers are P7 capture primers.

15. The composition of claim 14, wherein the capture primers of the first plurality of capture primers are shortened P5 capture primers, and wherein the orthogonal capture primers of the second plurality of orthogonal capture primers are shortened P7 capture primers.

16. The composition of claim 13, wherein the capture primers of the first plurality of capture primers are approximately the same length as the orthogonal capture primers of the second plurality of capture primers.

17. The composition of claim 13, wherein the capture primers of the second plurality of capture primers are approximately the same length as the orthogonal capture primers of the first plurality of capture primers.

18. The composition of claim 1, wherein the first region of the substrate is adjacent to the second region of the substrate.

19. The composition of claim 1, wherein the first region of the substrate surrounds the second region of the substrate.

20. The composition of claim 1, wherein the second region of the substrate surrounds the first region of the substrate.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aatgatacgg cgaccaccga                                                    20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caagcagaag acggcatacg a                                                  21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3 tttttcaag cagaagacgg c                                                   21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttttaatga tacggcgacc a                                                  21
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcggtggtcg ccgtatcatt                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cacatctaga gccaccagcg                                                   20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcgtatgccg tcttctgctt g                                                 21

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tagagcatac ggcag                                                        15
```